United States Patent [19]
Yan

[11] Patent Number: 5,856,928
[45] Date of Patent: Jan. 5, 1999

[54] GENE AND PROTEIN REPRESENTATION, CHARACTERIZATION AND INTERPRETATION PROCESS

[76] Inventor: Johnson F. Yan, 3801 SW. 326th St., Federal Way, Wash. 98023-2611

[21] Appl. No.: 559,248

[22] Filed: Nov. 16, 1995

Related U.S. Application Data

[63] Continuation-in-part of Ser. No. 74,180, Jun. 9, 1993, abandoned, which is a continuation of Ser. No. 54,455, Apr. 28, 1993, abandoned, which is a continuation-in-part of Ser. No. 850,754, Mar. 13, 1992, abandoned.

[51] Int. Cl.$^6$ .............................. G06F 17/30; G06F 19/00
[52] U.S. Cl. .......................... 364/496; 364/578; 395/603; 395/611
[58] Field of Search .................................... 364/496, 497, 364/578; 395/603, 611

[56] References Cited

U.S. PATENT DOCUMENTS

| | | | |
|---|---|---|---|
| D. 313,625 | 1/1991 | Yan et al. | D19/62 |
| 4,895,802 | 1/1990 | Sone et al. | 435/172.3 |
| 4,956,281 | 9/1990 | Wallner et al. | 435/69.3 |
| 5,030,570 | 7/1991 | Breakerfield et al. | 435/189 |
| 5,030,722 | 7/1991 | Snyder et al. | 536/23.5 |
| 5,070,101 | 12/1991 | Kaminski | 514/399 |

OTHER PUBLICATIONS

Yan, Johnson F., et al., Prime Numbers and the Amino Acide Code: Analogy in Coding Properties:, J. theo. Biol. (1991) 151, 333–341.
Blaisdell, B. Edwin, "choice of Base at Silent Codon Site 3 is not selectively Neutral in Eucaryotic Structural Genes: It Maintains Excess Short Runs of Weak and Strong Hydrogen Bonding Bases", *J Mol Evol* (1983) 19:226–236.
Eigen, Manfred, et al., "How old is the Genetic Code" Statistical Geometry of tRNA provides an Answer, *Science* vol. 244, 12 May 1989, 673–679.
Gamow, g. (1954) *Nature* 173, 318., No Date.
Glenn, J.A., *Dictionary of Mathematics*, p. 159., No Date.
Hardy, G.H. *A. Mathematician's Apology*, p. 97 and 123, No Date.
Hendry, L.B., et al., "First Approximation of a Sterochemical Rationale for the Genetic Code based on the Topography and Physiocochemical Properties of 'cavities' Constructed from Models of DNA", *Proc. Natl. Acad. Sci. USI*, 78, No. 12, pp. 7440–7444, Dec. 1981.
Niven, Ivan et al., *An Introduction to the Gheory of Numbers*, pp. 103–105., No Date.
Ohno, Susumo, "Grammatical Analysis of DNA Sequences Provides a Rationale for the Regulatory Control of an Entire Chromosome", proceeding of the international symposium on Origin of Life, Mar. 1990.
Ohno, Susumu et al., "The Primitive Code and Repeats of Base Oligomers as the Primordial Protein–encoding Sequence", *Proc. Nat'l . Acad. Sci., USA*, vol. 80, pp. 3391–3395, Jun. 1983.
Ohno, Susumu et al., "The All Pervasive Principle of Repetitious Recurrence Governs Not Only Coding Sequence Construction But Also Human Endeavor in Musical Composition", *Immunogenetice* 24:71–78, 1986.
Stryer, Lubert *Biochemistry*, pp. 450, 505,509,514, No Date.
Swanson, Rosmarie, "A Unifying Concept for the Amino Acid code", *Bull, math. Biol.* 46, 187–203. No Date.
Woese, Carl R., *The Genetic Code*, "The Molecular Basis for Genetic Expression", No Date.
Yan, Johnson F., *DNA and the I Ching*, No Date.

*Primary Examiner*—Ellis B. Ramirez
*Assistant Examiner*—M. Kemper
*Attorney, Agent, or Firm*—Suiter & Associates PC

[57] ABSTRACT

Natural numbers are assigned to represent DNA and mRNA nucleotide bases (n-numbers 0, 1, 2, 3), base pairing numbers in RNA (p-numbers 0, 1, 2, 3), and amino acids in protein (z-numbers with seventeen prime numbers and odd numbers 1, 25, 45; all smaller than 64). These numbers reflect intrinsic properties of the nucleotide bases, their triplet-base codon combinatorics and chemical bonding properties (hydrogen bonds, hydrophobicity, codon positions, and molecular sizes). Gene and protein sequences may be represented, characterized and interpreted by their specific n-sums and z-sums. Base dimers/oligomers and dipeptides/oligopeptides are found to correspond to their sums, as verified by using statistical and other methods. Utility rules are devised for applications in base dimers distribution, RNA base pairing, oligomer repeats and the encoded oligopeptide repeats. Conserved base pairs in four stems of a given mitochondrial tRNA correlate well with the z-number in the encoded hydrophobic amino acid. Conserved protein segments are mostly prime peptides (oligopeptides with prime number z-sums) except those with strict repeats (collagen Gly-3 repeats, leucine zipper Leu-7 repeats, etc.). This representational scheme is also capable of inferring protein folding and cross linking. Sequence alphabets (nucleotide bases and amino acids) in existing and future data banks can be converted to such numbers to facilitate computation and characterization.

14 Claims, 8 Drawing Sheets

```
                                          (T)
gpm GPS gpr glp gpP GAp gpq gfq gpp gep (30)
                                          c
geP gaS gpm gpr gpp gpp GKN gdD GEa gkp (60)

grp GEr gpp gpq GAr glP gtA glp GMk ghr (90)
    (T) (T)
gfS GLd gak gdA GPA gpK geP GSp GEn GAp (120)
     c   D
GQm gpr glp GEr grP GAp GPA GAR GNd gat (150)
    (G)                             (T) (T)
GAA gpp GPT GPA gpp gfp gav gaK GEA gpq (180)
     r                               c   c
                                    (C)
gpr GSe gpq GVR gep gpp GPA GAA GPa gnP (210)
               (T)                   c
gaD gqP gak gan GAp giA GAp gfP GAr GPS (240)
    (C)          c  (T)
gpq gpg gpp gpK GNS geP GAP GSk GDt gaK (270)
     C               V
gep gpv gvq gpp GPA GEE gkR GAR gep GPT (300)

glp gpp GEr ggP GSr gfP gad gvA gpk GPA (330)

GER GSp GPA gpK GSp GEA grp GEA glP gak (360)
                               (T)
GLt GSP GSp gpd GKT gpp GPa gqd grp gpp (390)
(C)                             c  (C)
gpP GAr gqa gvM gfp gpk GAA gep gkA GER (420)
R                                   c
gvp gpP gav GPa gkD GEA gaq gpp GPA GPA (450)

GER GEq GPa GSp gfQ glp GPA gpp GEa gkp (480)

geq gvp GDL GAp GPs GAR GEr gfp GER gvq (510)
```

FIG. 3A

```
                    (C)
 gpp GPA gpR gan GAp GNd gak gdA GAP GAP (540)
(T)         (A)       c (T)     (T)
 GSQ GAp GLQ gmp GER GAA glp gpk gdr gdA (570)
  D           R           D       S (T)
 gpk gad GSp gkd GVr GLT gpi gpp GPA GAp (600)
                                      S
 gdK GES GPS GPA GPt GAR GAp gdR gep gpp (630)
(C)     (C)
 GPA GFA gpP gad gqP gaK gep gdA gak gdA (660)
  S       V
        (A)     (C)
 gpp GPA GPA gpp gpi GNv GAP gak GAR gsA (690)
          R       D
(T)                                 (C)
 gpP gat gfP GAA GRv gpp GPS gnA gpp gpp (720)
  C                                   C
                                    (T)
 GPa GKE ggk gpR geT GPA grp gev gpp gpp (750)
                                      C
 GPA GEK GSP gad GPA GAP GTp gpq g-ia gqR (780)
                                  *
 gvv glp gqR GEr gfp glp GPS gep gkq GPS (810)
                            (T)
 gaS GEr gpp gpm gpp GLA gpp GES GRE GAP (840)
    (T) (A)                   s
 GAE GSp grd GSP gak gdR geT GPA gpP GAP (870)
      S   R     (C)
 GAP GAp gpv GPa GKs gdR geT GPA GPA gpv (900)
     000          D
    (C)         (C)                 (C)
 GPA GAr GPA gpq gpr gdK get GEq gdr gik (930)
      C           S                   A
 ghr gfS GLq gpp gpP GSp GEq GPs gaS GPA (960)
    (C)         (C) (A)             (T)
 gpr gpP gsA GAp gkD GLN glp gpi gpp gpr (990)
      S           V   R               C
                (C) (A) (T)
 GRT gdA gpv gpp gpp gpp gpp gpp (sag)    (1014)
                  S   V   S
                          V
```

FIG. 3B

| Period -> A | B | C | D | E | F |
|---|---|---|---|---|---|
| I. MDAIKKk | MQMLKLD | Kenaldr | AEEAEAD | KKAAEdr | SKQLEde |
| II. LVSLQKK | LKGTEDE | LDKYSEA | LKDAQEK | Lelaekk | ATDaead |
| III. VASLNrr | IQLVEEe | LDRAQer | Latalqk | LEEAEKA | Adeserg |
| IV. | MKVIesr | Aqkdeek | MEIQEIQ | LKEakhi | AEDADRK |
| V. YEEvark | LVIIESD | LERaeer | Aelsegk | | CAELEee |
| VI. LKTVTNN | LKSleaq | AEKYSqk | | | |
| | | EDKYEEE | IKVLSDk | LKEakhi | Aefaers |
| VII. VTKleks | Iddlede | Lyaqklk | YKAISEe | Ldhalnd | MTSi--- |

FIG.4

|     | NO. 1 |         |         |     | NO. 2  |         |          |     |
|-----|-------|---------|---------|-----|--------|---------|----------|-----|
| GL1 | ISgvag | LGGFLfg | FDTAVIn |     | Lsvslal | LGSalga | FGAgp   | Ia  |
| GL2 | ICVGvfva | VGGflfg | VDTGLIn |   | ILVSFLs | LGTffga | LTAPF   | IS  |
| GL3 | MLAvggav | LGSLQFG | Vntgvin |   | LWSlsva | IFSVgg  | MIGSFSVG | LFV |
| GL4 | FTVFTav | LGSFQfg | YDIGVIN |    | MLWSLSV | SSFavgg | MVASFfg | GWL |
| GL5 | Lavfsav | LGSLQFG | Ynigvin |    | LWALSVA | IFSVggm | ISSFLIGI | IS  |
|     |       | *   ** | **      |     |        | *       |          |     |

|     | NO. 3  |         |          |     | NO. 4   |          |        |     |
|-----|--------|---------|----------|-----|---------|----------|--------|-----|
| GL1 | MIlaav | LFTlss  | Igsglpf  |     | ifwrvlgg | IGVGAAsv | Iapay | Ia  |
| GL2 | IIFst  | IFIFS   | IGNSLQVG |     | IVgrv   | ISGIGIGA | ISAVVP | LYQa |
| GL3 | MLMMNLL | Afvsavl | MGFsklg |     | ILgrfi  | igvycg   | LTTGFVP | Myvg |
| GL4 | MLAANsl | SLTGALL | MCGskfg |     | IAGRSVSG | Lycgl   | ISQLvp | MYIG |
| GL5 | MLAnnvl | AVLGGal | MGLANAA* |    | ILgrfl  | IGAYSGLT | SGLvp | Myvg |
|     |        |         | *        |     | *   *   |          |        |     |

|     | NO. 5  |        |         |     | NO. 6  |         |         |
|-----|--------|--------|---------|-----|--------|---------|---------|
| GL1 | GSLqqla | IVsgif | ALLSNwf |    | MFWtel | Ipallyg | VCAFLip |
| GL2 | ISTYqwa | ITWGLL | VSSAVSQ |    | IPIGLQY | VWSsfla | Igmfflp |
| GL3 | GTLHQLG | IVvgil | Iaqvfgl |    | LLLSIIF | Ipallqc | IVLPfcp |
| GL4 | GTLHQla | Lvtgil | ISqiagl |    | ILLGlsa | VPAllqc | LLLLFCP |
| GL5 | GTLNQla | IVigil | VAQvlgl |    | Lllaitv | LPAllql | LLLPFcp |
|     | *      | *      |         |     |        |         | *       |

FIG. 5A

|     | NO. 7    |        |         | NO. 8   |         |         |
| --- | -------- | ------ | ------- | ------- | ------- | ------- |
| GL1 | IGMGLS   | ALQqfvg | INVIFYY | ITvitgf | INILTTL | VAIAfv  |
| GL2 | MFTGIAlq | AFQqfsg | INFIFYY | Lvsfity | AVNVVFN | VPGLFFV |
| GL3 | IAVVLQ   | LSQQLSG | INAVfyy | YATIGSg | IVNTAF  | TVVSLFV |
| GL4 | IVVALMlh | LAQQFSG | INGIFyy | ISqpvyat | Igvgain | MIftav  |
| GL5 | IIAVVlq  | LSQQLSG | INAVfyy | YATIgag | VVNTVf  | TLVSVLL |
|     |          | * *  * | * * * * *|         |         |         |

|     | NO. 9  |         |         | NO. 10  |         |         |
| --- | ------ | ------- | ------- | ------- | ------- | ------- |
| GL1 | Mgs ig | Mtitlg  | ILgqptl | LVTANly | VFSFGfs | wgpivwv |
| GL2 | Vlvvggv | IMTIANF | IVAIVgc | IAFIClf | iaafsat | wggvvwv |
| GL3 | Igla g | Magcail | MTIALALL | IVaifgf | Vaffevg | PGPIPWf |
| GL4 | LAGMIG | MFFCAvf | MSLGLvl | MTAiflf | VSFFEIg | PGPIPWf |
| GL5 | Igla g | MCGca   | ILmtval | IVaifgf | Vaffeig | PGPIPWf |
|     |        | *       |         |         | *       | *   *   |

|     | NO. 11 |         |         | MO. 12  |         |         |
| --- | ------ | ------- | ------- | ------- | ------- | ------- |
| GL1 | ALSVAAG | EQWianf | IISTTfp | Lgpaygl | YATsaa  | ISIFFiw |
| GL2 | CTAicaa | Anwlvnf | ICALITP | LGAkiff | IWgslna | MGVIvvy |
| GL3 | IAVAgf  | SNWtsnf | IVGMCFQY | cgpyvfi | IFTVLLv | LFFifty |
| GL4 | ALALAAF | SNWVCNF | IIALCFQ | Lgpyvff | LFAGVvl | VFTLFtf |
| GL5 | MAVAGf  | SNWTCNF | IVGMGF  | Mgpyvfl | Lfavlll | GFFIftf |
|     |         | *  ** * |         | *       |         |         |

FIG. 5B

| | | | |
|---|---|---|---|
| MANLSYW (157') | LLALFVA (223') | Mwtdvgl (159) | CKKRPkp (129) |
| MANLGCW (191') | MLVLFVA (197') | TWSDLgl (161) | CKKRPkp (129) |
| | | | |
| GGWNTgg (261 ) | SRYPGQG (263') | SPGgnry (255) | PPQGGGT (233') |
| GGWNTgg | SRYPGQG | SPGgnry | PPQGGgg (289) |
| | | | |
| WGQPHGG (263') | GWGQPHG (263') | GGWGQPH (263') | GGGWGQP (277') |
| WGQPHGG | GWGQPHG | GGWGQPH | GGGWGQP |
| ++++-++ | +++++-+ | ++++++- | +++++++ |
| | | | |
| HGGGWGQ (311') | gggthnr (265 ) | WNKPSkp ( 81) | KTNMKHM (83') |
| HGGGWGQ | GGGTHSQ (283') | WNKPSkp | KTNMKHM |
| -++++++ | +++-- | | |
| | | | |
| AGAaaag (387) | AVVGGlg (335) | GYMlgsa (267) | Msrpmmh (135) |
| AGAaaag | AVVGGlg | GYMlgsa | Msrpiih (133) |
| | | | |
| FGNdwed (219) | RYYRENM (233') | nrypnqv (175 ) | YYRPVDQ (227') |
| fgsdyed (279) | RYYRENM | HRYPNQV (211') | YYRPMDE (229') |
| | | | |
| YNNQNNF (131') | VHDCVNIT (223') | IKQHTVTT (131') | TTKGENF (173') |
| YSNQNNF (149') | VHDCVNIT | IKQHTVTT | TTKGENF |
| -+--+ | --+0--0- | 0++----- | --++--+ |
| | | | |
| TETDIKi (111 ) | MERVVeq (259) | MCTTQYQ (139') | KESQAyy (253) |
| TETDVKM (151') | MERVVeq | Mcitqy (117) | Eresqay (299) |
| ---+ | | | |
| | | | |
| DGRRSSA (277') | VLFSSPP (167') | VILLIsf (133 ) | LIFLmvg (166) |
| Yqrgssm (221 ) | VLFSSPP | VILLIsf | LIFLivg (165) |

FIG. 6

GENE AND PROTEIN REPRESENTATION, CHARACTERIZATION AND INTERPRETATION PROCESS

CROSS REFERENCE TO RELATED APPLICATION

The present application is a continuation-in-part of U.S. application Ser. No. 08/074,180 filed Jun. 9, 1993, now abandoned which in turn is a continuation of U.S. patent application Ser. No. 08/054,455 filed Apr. 28, 1993, now abandoned which in turn is a continuation-in-part of U.S. patent application Ser. No. 07/850,754 filed on Mar. 13, 1992 now abandoned.

TECHNICAL FIELD

The present invention is directed to coding schema and the like and more particularly to numeric coding methods for gene and protein sequence representation, characterization and interpretation.

BACKGROUND OF THE INVENTION

In 1967, Woese classified methods of interpreting the genetic (or amino acid) code in mechanistic and stochastic models. In his mechanistic model Woese attempted a molecular geometrical fit between codons and their coded amino acids. One of the first attempts at such a code was the "diamond" code proposed by Gamow in 1954. As recently as 1981, when the actions of tRNA and rRNA in the synthesis of protein were already well-known, the geometrical method still attracted attention, as typified by the work of Hendry et al. (1981) who drew a structural analogy between codons and amino acids. However, the lack of any direct contact between DNA or mRNA with protein molecules rendered "lock and key" models impotent as predictors of coding mechanisms.

Gamow's attempt is an admirable one, because, although his "diamond" geometry was discredited by later observation, he did offer a combinatorial schema motivated by the few numbers available at that time, i.e., four nucleotide bases, 64 triplet-base codons with only 20 amino acids. Unfortunately his combinatorics and geometry could not be separated from each other, and the combinatorial part suffered the same fate as his proposed geometric model.

DISCLOSURE OF THE INVENTION

The coding scheme herein described assigns discrete numbers to nucleotide bases, codons and amino acids. In a strictly combinatorial way, molecular factors such as mechanism and geometry are incorporated into such numbers, which are implicitly included in the information on upstream base properties and downstream protein. Combinatorial specificity allows for the translation of coding properties into the properties of numbers, and vice versa.

In living cells, genetic information is passed from DNA to messenger RNA ("transcription") which in turn provides the information for the synthesis of protein ("translation"). The information is inscribed in the nucleotide bases—A, C, T, G in DNA and A, C, U, G in RNA. Genes are long stretches of DNA bases that are stored in a double-helix form. Proteins are polymers of amino acids. There are 20 naturally occurring amino acids encoded by DNA and mRNA. The translation of four nucleotide bases A, C, T(U), G to twenty amino acids is made through the genetic code (or the amino acid code, Table 1).

TABLE 1

The Genetic Code

| | | | |
|---|---|---|---|
| AAA: Lys | AAC: Asn | AAU: Asn | AAG: Lys |
| ACA: Thr | ACC: Thr | ACU: Thr | ACG: Thr |
| AUA: Ile (Met) | AUC: Ile | AUU: Ile | AUG: Met |
| AGA: Arg (Stop) | AGC: Ser | AGU: Ser | AGG: Arg (Stop) |
| CAA: Gln | CAC: His | CAU: His | CAG: Gln |
| CCA: Pro | CCC: Pro | CCU: Pro | CCG: Pro |
| CUA: Leu | CUC: Leu | CUU: Leu | CUG: Leu |
| CGA: Arg | CGC: Arg | CGU: Arg | CGG: Arg |
| UAA: Stop | UAC: Tyr | UAU: Tyr | UAG: Stop |
| UCA: Ser | UCC: Ser | UCU: Ser | UCG: Ser |
| UUA: Leu | UUC: Phe | UUU: Phe | UUG: Leu |
| UGA: Stop (Trp) | UGC: Cys | UGU: Cys | UGG: Trp |
| GAA: Glu | GAC: Asp | GAU: Asp | GAG: Glu |
| GCA: Ala | GCC: Ala | GCU: Ala | GCG: Ala |
| GUA: Val | GUC: Val | GUU: Val | GUG: Val |
| GGA: Gly | GGC: Gly | GGU: Gly | GGG: Gly |

Shown in Table 1 are two major versions of the genetic code, the universal code and the mitochondrial code (variances from the universal code shown in parentheses).

Underlined amino acids are those having non-prime "amino acid numbers" (see below). Bolded are the eight quartets of nucleic acids for which the first two codons determine the identity of the amino acid (see below.)

The present invention discloses a novel numerical method adapted to analyze the sequence language of nucleic acid and protein. This method involves the translation of nucleotide bases into quaternary number units ("n-numbers"—0, 1, 2, 3) and amino acids into a unique set of natural numbers ("z-numbers"—seventeen prime numbers and three odd numbers smaller than 64). The assignment of both n- and z-numbers is specific to each nucleotide base and each amino acid residue. Specifically, they are summarized as follows:

TABLE 2 n-numbers and z-numbers n-numbers: A = 0, C = 1, T(U) = 2, G = 3
z-numbers: Stop codon = 0

| | | | |
|---|---|---|---|
| Trp(W) = $\underline{1}$, | Ile(I) = 2, | Met(M) = 3, | Thr(T) = 5 |
| Lys(K) = 7, | Asn(N) = 11, | Pro(P) = 13, | Leu(L) = 17 |
| Gln(Q) = 19, | Ser(S) = 29, | Asp(D) = 31, | Arg(R) = 37 |
| Val(V) = 41, | Tyr(Y) = 43, | His(H) = 47, | Ala(A) = 53 |
| Glu(E) = 59, | Gly(G) = 61, | Phe(F) = $\underline{25}$ | Cys(C) = $\underline{45}$ |

In Table 2, the amino acids are written in both three-letter and single-letter notations. The non-prime (underlined) z-numbers are assigned to amino acids Trp, Phe and Cys that probably evolved last among the twenty.

The present invention discloses a method based on the properties of the z-numbers which are analogous to the coding properties in a subtle and elegant way: Let i, j, k, denote the n-numbers of the first, second, and third codon bases, then z<64 can be expressed as a function of i, j and k; that is, z=f(i, j, k). These Diophantine equations allow only positive integral (natural number) solutions.

The conventional method in analyzing biomolecular sequences and structure emphasizes molecular geometry as introduced by Pauling and Corey (U.S. Pat. No. 3,510,961). The Pauling-Corey model is built from small molecules and extended to macromolecules. Model building can also be demonstrated with computer graphics. Unfortunately, biomolecular sequences involve huge numbers of possible combinations of nucleic acid or amino acid residues. The computation of their coordinates, interatomic distances and energies of interaction present a formidable task even for supercomputers. Furthermore, the geometrical computation is mainly concerned with secondary or tertiary structures. The Pauling-Corey model fails to explain the primary structure (or sequence), "connectivity" or "strategy" of growth of these biopolymers. Thus, a new approach is necessary.

Molecular sequences are also studied by comparing with some abstract forms of human senses, for example, language and music. While these methods help to demonstrate the analogies qualitatively, they do not lend themselves to detailed analysis and manipulation.

In contrast to the visual or auditory form of senses (or levels of abstraction), natural numbers offer an abstraction of "pure thought". Senses and thought are the input and output of the cognitive process. In a theoretical article, Heschl claimed that L (Life)=C (Cognition). The study on the properties of natural numbers is called "number theory" which is also the purest form of "pure mathematics". Conventional mathematics using continuous numbers has been replaced with discrete mathematics in quantum theory. Continuous mathematics is unfit for biomolecular property sequence description since all basic number properties (odd/even, prime/composite) are lost in continuous numbers.

OBJECTS OF THE INVENTION

Therefore, it is a principal object of the present invention to provide a numeric coding method to represent, manipulate and analyze gene and protein sequences.

Another object of the present invention is to provide a numeric coding method for gene and protein sequencing which is useful in characterizing the relationship between nucleic acid bases and amino acids as well as DNA and protein sequences.

Another object of the present invention is to provide a numeric coding method for gene and protein sequence representation which provides a unique intrinsic representation of nucleic bases and amino acids.

Another object of the present invention is to provide a numeric coding method for gene and protein sequences which provides a process for cross-comparison of the coding properties of the non-overlapping triplet-base codons prescribed by the genetic and the amino acid codes.

Another object of the present invention is to provide a numeric coding method for protein sequences which provides means for characterizing oligopeptides.

Another object of the present invention is to provide a numeric coding method for gene sequences which provides base dimer frequency data characteristics.

Another object of the present invention is to provide a numeric coding method for gene and protein sequences which provides means for determining the secondary structure of RNA.

Another object of the present invention is to provide a numeric coding method for gene and protein sequences which provides means for identifying non-coding hexamer repeats (telomeres) which are known to cap chromosome ends.

Another object of the present invention is to provide a numeric coding method for gene and protein sequences which provides means for determining the amino acid heads of conserved prime oligopeptides, fixed length Gly-3 tripeptides (collagen), and Leu-7 heptapeptides.

Another object of the present invention is to provide a numeric coding method for gene and protein sequences which provides means for determining the order of conservativeness and the probability of DNA oligomers and prime peptides.

Another object of the present invention is to provide a numeric coding method for gene and protein sequences which provides means for evaluating abundant prime peptides in proteins.

Another object of the present invention is to provide a numeric coding method for gene and protein sequences which provides means for determining mutational hot spots in genes and proteins potentially causing genetic diseases.

Another object of the present invention is to provide a numeric coding method for gene and protein sequences which provides means for effective design of peptide and protein drugs.

Another object of the present invention is to provide a numeric coding method for gene and protein sequences which provides means for determining sequence specificity, compatibility and connectivity in genes and proteins.

Another object of the present invention is to provide a numeric coding method for gene and protein sequences which provides means for detection, alignment and comparison of homologous protein sequences.

Finally, another object of the present invention is to provide a numeric coding method for gene and protein sequences which provides information regarding codon usage in the hextet-coded amino acids. These and other objects will be apparent to those skilled in the art.

BRIEF DESCRIPTION OF THE DRAWINGS

FIG. 3A and 3B are sequence listings of the collagen α1(I) chain (human). This sequence data is taken from Bernard et al. (1983) and Tromp et al. (1988); mutation data from Kuivaniemi et al. (1991). (Capital letters head prime tripeptides; *=bond cleavable by mammalian collagenase; 000= deletion of three bases; and underlined are tripeptide runs. See text for other symbols;

FIG. 4 are sequence listings of tropomyosin data taken from McLachlan et al. (1975). Capital letters denote prime heptamers, hexamers, pentamers, tetramers, etc., summing z-numbers from the first residue in each heptad, for example, in I(B), MQMLKLD is a prime heptamer; in I(B) KKAAEdr has a prime pentamer; and in I(C), Kenaldr, only the first residue is a prime, the heptamer is nonprime;

FIGS. 5A and 5B are sequence listing of twelve membrane spanning segments of five glucose transport proteins, data taken from Henderson (1990). Alignment is made with Ile and Met as first residues in heptads and maximum chance for prime peptides (shown in capital letters). * denotes complete alignment; and FIG. 6 is a sequence listing of the continuous Heptad Scan of prion proteins (PrP). Sequence data taken from Gabriel et al. (1992). First line: Hamster PrP, 254 residues, 36 heptads, 19 primes. Inside parentheses are the z-numbers of the heptads, they are marked with a prime sign (') to denote primes.

SUMMARY OF THE INVENTION

Figure 1:
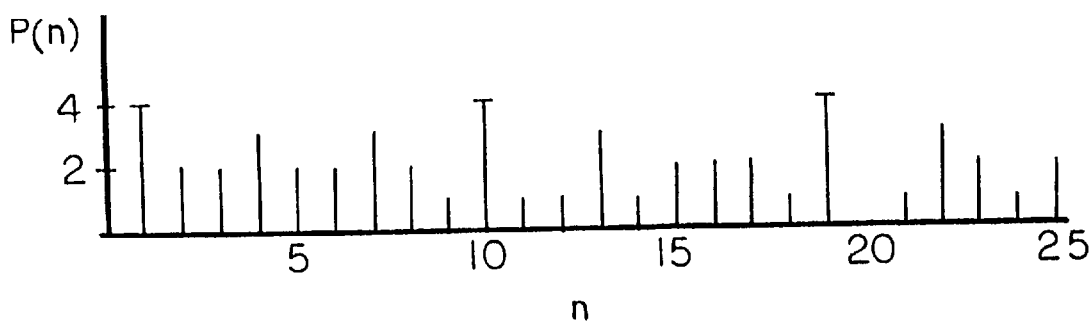
FIG. 1 is a graphical representation of the number of primes in the range of 10n and 10(n+1) wherein said numbers equal P(n)

The present invention teaches a novel process for representing and evaluating protein and gene sequences. The genetic code is a quaternary code. Comparison with other binary or quaternary codes has been attempted. In addition to the structural analogy described above (Hendry et al., 1981), analogies between DNA sequences and language or music (Ohno & Ohno, 1986) may also assist in illuminating a workable coding strategy. The combinatorial method described here, however, associates more specifically the four bases in mRNA or DNA with the four quaternary units (0, 1, 2, 3), by making use of the information generating properties of prime and odd numbers.

The simplest way of expressing natural numbers is in the binary form with units 0 and 1. Information is generated by both units but 1 is more "information-creative", in a sense that 1 must appear at least once in any string of binary presentation. For example, 000000 gives no information but 000010 and 111111 are non-zero information. In the binary system of numbers, 1 and 0 in the last digit manifest as odd and even numbers, respectively. Thus odd numbers are more "creative" than even numbers. Additively generated numbers can be primes or non-primes. Multiplicatively generated numbers are non-primes ("composites" in number theory terminology). Thus, prime numbers are considered more creative than non-primes in number theory.

More than 2000 years ago Euclid regarded a number as a "line interval compounded of units, and a prime as a number which can only be measured by the unit" (not itself a number) (Glenn & Littler, 1984). The creativeness and indivisibility of prime numbers permit the inference that primes smaller than 64 are the number equivalents of amino acids; or that amino acids are such Euclid units of living molecules.

To identify the quaternary units to the nucleotide bases, it is noted that the only discrete molecular properties are the three hydrogen bonds in G:C pairs, two H-bonds in A:U(T) pairs. Thus, G and C are the odd-number or strong-bonding units (1 and 3); A and U are the even (weak-bonding) units (0 and 2). Furthermore, poly-A tails are usually attached to mRNA after a stop signal, without coding amino acids. This means that base A serves as a "blank", its number equivalent is 0. The "creativeness" of the quaternary units runs in the order:

$$1>3>2>0. \tag{1}$$

It is well-known that the second (middle) position in a codon is the most dominant one in determining the coding strategy. In the genetic code, of the eight sets of synonymous quartets represented in bold in Table 1 (each quartet codes for a single amino acid in the degenerate DNA code), there are four sets with a middle-C. This means that base C is the most creative. The above arguments lead to a unique set of "nucleotide numbers" (Yan, 1991):

$$A=0, C=1, U(T)=2, G=3. \tag{2}$$

Assignments of nucleotide numbers appearing in the literature are mostly arbitrary. Those closest to (2) are: Swanson's (1984) assignment differs from (2) in that A=2 and U=0, which satisfies the strong- and weak-bonding argument but not the "creativeness" discussed above. In an analogous comparison with music, Ohno & Ohno (1986) assign the order A, G, U, C with rising musical scale, which appears to be a decreasing numerical order 4, 3, 2, 1. The number 4 has a quaternary remainder of 0. Thus, the assignment in (2) can be considered as in agreement with that of Ohno & Ohno.

Based on the above number equivalence of nucleotide bases, we seek an "amino acid number" (z) such that z<64 and that a Diophantine equation $$z=f(i,j,k),$$

holds for the nucleotide numbers i, j and k of the first, second and third codon bases, respectively. Obviously, the choice of nucleotide numbers is crucial for the assignment (coding) of z.

Rule 1. In general, to be information-creative to code for an amino acid, z must be an odd number, or a prime, or both. In particular, the first odd number (1) and the only even prime (2) should be used as an AA number. The "stop" codons are assigned as 0.

In number theory, prime numbers can further be classified as those having quaternary remainder 1 (prime numbers in the form 4n+1) and those having quaternary remainder 3 (the 4n+3 form). These have been designated herein as the P1 and P3 numbers, respectively. Hardy (1969) paid special attention to the P1 primes because they can be expressed as unique sums of two squares. There are eight such P1 primes between 0 and 63. From both the universal and mitochondrial genetic codes, one observes that eight synonymous quartets (with 32 codons) are determined uniquely by the first two codon bases. This combinatorial specificity yields the following rule:

Rule 2. (The P1 rule). All P1 primes smaller than 64 and specified by two-square sums are the number equivalents of the eight quartets of degenerate synonymous codons in which the amino acid is specified by the first two bases of the three codon positions.

The 64 codons are divided into four groups, with the first two groups composed of eight synonymous quartets. For the synonymous quartets, the P1 numbers are the sums of a square of an odd number, and a square of an even number. The "odd" and "even" squares are equivalent to the "first" and "second" positions in these codons. In other words, $$z=(2i+1)^2+(2j)^2. \tag{3}$$

In this equation k is equal to zero since its identity is insignificant. This is a form of Diophantine equations (Niven & Zuckerman, 1972), which allow only positive-integer solutions.

GROUP I. CODONS (MIDDLE-C)

Because of the condition z<64, Eqn. (3) holds only for middle-C codons, i.e., only j=1 (C); i=0 (A), 1 (C), 2 (U), 3 (G) are allowed. This may be called the "selection rule" for this set of quartets. The four quartets and their "quartet numbers" are shown in Table 3.

In Table 3, since each "quartet set" codes for one amino acid, the quartet numbers are also the amino acid numbers.

TABLE 3

| Quartet Nº | Middle-C quartets Synonymous codons[†] | Amino acid |
|---|---|---|
| $1^2 + 2^2 = 5$ | ACX | Thr |
| $3^2 + 2^2 = 13$ | CCX | Pro |
| $5^2 + 2^2 = 29$ | UCX | Ser |
| $7^2 + 2^2 = 53$ | GCX | Ala |

[†]Letter X denotes any base (A, C, U, G).

GROUP II. CODONS (OTHER SYNONYMOUS QUARTETS)

There are four other synonymous quartets, each of which contain no A in the first two positions, and no C in the second position: CUX (Leu), GUX (Val), CGX (Arg) and GGX (Gly). But in this case, the odd number term in (3) is changed to the form (2i-1) to exclude the base A from the first position. The change of the odd square form does not break the P1 rule. For synonymous quartets other than those with middle-C:

$$z=(2i-1)^2+(2j)^2 \quad (4)$$

The selection rule is given by i=1, 3; and j=2, 3. These quartets are listed in Table 4.

All P1 primes smaller than 64 are uniquely used by the quartet numbers in group I and group II. That these equations allow the unique assignment of all P1 primes smaller than 64 to the eight exigent quartets of degenerate codons suggests the P1 rule is consonant with an underlying constraint in the DNA coding "strategy".

TABLE 4

Other quartets [eqn (4)]

| Quartet № | i | j | Quartet codons | Amino acid |
|---|---|---|---|---|
| 17 | 1 | 2 | CUX | Leu |
| 37 | 1 | 3 | CGX | Arg |
| 41 | 3 | 2 | GUX | Val |
| 61 | 3 | 3 | GGX | Gly |

GROUP III. OTHER MIDDLE-U AND MIDDLE-G CODONS

Conditions for the assignment of this group are not as strong as the first two groups.

In most cases, a quartet is split into two doublets, for example: UUX is divided into UUR (Leu) and UUY (Phe), where R=purines (A or G); Y=pyrimidines (C or U). In this group the doublets are mostly "carry-overs" of the hextet codons. Difference between two versions of the genetic code (the universal and mitochondrial) also appears in this group of codons.

The AA numbers of Ser (29) and Arg (37) have already been assigned for groups I and II, specificity requires that they retain the same numbers in group III doublets (AGR and AGY) in the universal genetic code.

Quartets of the form AUX and AGX are excluded from the relationship prescribed by eqn (4) because 2i−1<0 is not allowed in a Diophantine equation. But quartets UUX and UGX, with middle-U or middle-G, can also be expressed as two-square sums:

UUX  $3^2 + 4^2 = 25$

UGX  $3^2 + 6^2 = 45$.

However, 25 and 45 are the only two non-prime odd numbers in the range between 0 and 63 obeying the "two-square" (but not P1) rule. These non-prime odd numbers are coding for the amino acids that act as "precursors" for some late amino acids, as discussed below.

The quartet UUX splits into UUR (code for Leu) and UUY (Phe). But Leu has an AA number=17 as determined in group 11 codons, and Leu is a very stable amino acid side chain. Thus, the non-prime number 25 is assigned to Phe, which is the precursor of Tyr. The quartet UGX is split into UGY (Cys) and UGR (Trp) but UGA=0 in the universal genetic code.

In an evolutionary sense, five of the 20 natural amino acids are "late" comers because they were biochemically synthesized from the other five "early" precursors, including the Phe→Tyr conversion (Stryer, 1975):

"Early" precursors and their "late" amino acids:

$$\begin{align} Cys\ +\ Asp &\longrightarrow Met \\ Asp &\longrightarrow Asn \\ Glu &\longrightarrow Gln \\ Ser &\longrightarrow Trp \\ Phe &\longrightarrow Tyr \end{align} \quad (5)$$

Since Cys, like Phe, is one of the precursors, it should take the non-prime number 45. The AA numbers for this group of codons discussed so far are given in Table 5.

The above discussion on group III codons shows that the P1 rule (which automatically includes the two-square rule) is a strong one, for there are no exceptions. The square rule alone, however, is a weaker condition. The M numbers for UGR (Trp) and the quartet AUX will be deduced later.

TABLE 5

Group III codons

| | |
|---|---|
| AGY (Ser) = 29 | AGR (Arg) = 37 (universal code) |
| | (stop) = 0 (mitochondrial) |
| UUY (Phe) = 25† | UUR (Leu) = 17 |
| UGY (Cys) = 45† | UGA (stop) = 0 (universal) |

GROUP IV. MIDDLE-A CODONS

Codons with middle-A cannot be expressed as two-square sums, for the obvious reason that j=0 in Eqns. (3) and (4), and that this group of codons do not generate synonymous quartets. But z must be a prime number as suggested by rule 1. These remaining primes are of the P3 type (in the general form 4n+3). For six doublets in this group n is either an odd number or two times an odd number, i.e. the Diophantine equations used for these doublets are:

$$z=4(2i+1)+3 \quad (6a)$$

or $$z=8(2i+1)+3. \quad (6b)$$

The change of the factor from four to eight implies an extension from the (two-bit) quaternary to the (three-bit) octet systems. Codon bases furnish two bits of information: strong- or weak-bonding, purine or pyrimidine. The third binary bit or a "switch" between early/late, invoked for Phe and Cys above, is no longer supplied by coding bases but by the downstream protein. Without invoking further informational bits, the early/late binary bit is represented by eqn (6a/b). The index i takes the numbers 0, 2, 3; specific to the first-position bases A, U, G, respectively. In Table 4, the number 23 inside the square bracket is the number calculated from eqn (6a) but it is "overridden" by a strong "stop" signal (0). The other middle-A quartet CAX will be discussed later.

TABLE 6

Middle-A codons

| i (Base) | Early precursors [eqn (6a)] | Late amino acids [eqn (6b)] |
|---|---|---|
| 0 (A) | AAR (Lys) = 7 | AAY (Asn) = 11 |
| 2 (U) | UAR (Stop) = 0 [23] | UAY (Tyr) = 43 |
| 3 (G) | GAY (Asp) = 31 | GAR (Glu) = 59 |

In observing all the tables above, it will be noted that the difference in the AA numbers of XXY and XXR is always a multiple of 4, thus:

Rule 3. (The 4n rule). Differences in the AA numbers between XXY and XXR, the purine-pyrimidine differences in the third codon position, are 4n; with n=0 for groups I and II codons. This rule is violated only when the AA numbers 0 and 2 appear in a quartet row of codons.

QUARTETS AUX AND CAX

The remaining five numbers, 1 and primes 2, 3, 19, 47, can be uniquely identified with the unassigned amino acids coded by AUX and CAX. Of these, 1 is the only number that obeys the 4n rule with its pyrimidine counterpart Cys (45). Therefore, Trp takes the number 1:

UGR (Trp) = 1 (mitochondrial code)
UGG (Trp) = 1,     UGA (stop) = 0 (universal code).

Numbers 3 and 19 can be expressed in the form 8n+3, with n=0 and n=2, respectively. The factor 8 again suggests that these numbers should be used for the "late" amino acids. They are Met and Gln in these two quartets:

AUR (Met) = 3 (mitochondrial),     CAR (Gln) = 19

This leaves 2 for Ile and 47 for His:

CAY (His) = 47,        CAR (Gln) = 19
AUY (Ile) = 2,         AUR (Met) = 3 (mitochondrial)
AUY (Ile) = 2          AUA (Ile) = 2 (universal)
                       AUG (Met) = 3 (universal)

The choice of Ile=2 and Met=3 is made to account for the complete set of quaternary units/remainders, in the following way:

stop=0, Trp=1, Ile=2, Met=3.

Because Ile is also used as an alternate initiation codon in mitochondria (Ohno & Eppien, 1983), these four quaternary units cover all the "kinetic" codons ("start" and "stop") and the most bulky and hydrophobic amino acid Trp. All three are the most sophisticated amino acids appearing in asymmetrical quartet rows in the universal code. For other codons discussed above, the synonymous quartets follow exclusively the P1 number series, the doublets follow mostly the P3 series. An order of "creativeness", analogous to (1), also holds for AA numbers with quaternary remainders 0, 1, 2, 3. That is, P1>P3>2>0.

The complete list of the deduced AA numbers is shown in Table 7. There is a "one-to-one correspondence" between coding properties and the properties of AA numbers, down to the details of coding strategy, base pairing, and codon structure.

TABLE 7

Complete list of AA N°'s (z)

| 0 (stop) | 1 (Trp) | 2 (Ile) | 3 (Met) | 5 (Thr) |
|---|---|---|---|---|
| | 7 (Lys) | 11 (Asn) | 13 (Pro) | 17 (Leu) |
| | 19 (Gln) | 29 (Ser) | 31 (Asp) | 37 (Arg) |
| | 41 (Val) | 43 (Tyr) | 47 (His) | 53 (Ala) |
| | 59 (Glu) | 61 (Gly) | 25 (Phe) | 45 (Cys) |

Note: Numbers underlined are non-primes.

The analogous properties can be listed in the order from strong to weak conditions in the coding strategy:

| Number property | Coding property |
|---|---|
| 0 | Stop signal |
| PI numbers | Synonymous quartets |
| Non-prime 2-square sums | Early precursor amino acids |
| p3 numbers | Precursor/late amino acids |
| 4n rule | Third-position R/Y |
| Quaternary units | Trp and kinetic codons |

The basic binary characteristics (odd or even) are implicitly maintained: in generating information, nucleotide numbers, and codon positions. This is strictly a combinatorial interpretation of the genetic code. The numerical "specificity" and uniqueness discussed here also mean that no other assignments of nucleotide numbers can reach this number/coding analogy.

DISCUSSION

Hardy (1969) believed that mathematics or numbers exist "outside us". If numbers also existed before life, and hence before the genetic code, then the coding scheme probably followed a simple, established number pattern. The fact that only a few number properties (binary/quaternary units and remainders, and primes) are sufficient to deduce a unique number pattern for the genetic code attests to the natural elegance of the coding scheme. However, we simply accept the existence of numbers and the genetic code, and translate each to the other, without considering this kind of "chicken or egg" problem. But the inter-translation of numbers and the code naturally brings in an evolutionary implication.

Geometry is not explicitly considered in the present approach. Instead, molecular and evolutionary factors specific to codon positions are expressed in a "qualitative" binary form: odd or even numbers of hydrogen bonds, molecular sizes (R or Y), and early or late amino acids. Except the last binary classification (early/late), the former two are the ones used in the analysis of "runs" of strong- and weak-bonding bases (Blaisdell, 1983) and the statistics of R and Y in tRNA molecules (Eigen et al. 1989). The early/late binary furnishes a "time" factor in the genetic code; while the other two imply a "space" factor (geometry).

The language of DNA or RNA appears to adopt a repetition of base oligomers (Ohno & Ohno, 1986; Ohno & Epplen, 1983). This is one of the most plausible interpretations for the propagation of nucleotide chains; because the first grammatical rule of a language is a drastic reduction of potentially enormous information content to a manageable size (Ohno, 1990). At the "syllable" level of base dimers, Ohno and his co-workers discovered the rule of TG/CT/CA-excess and CG/TA-deficiency. The excessive dimers happen to have nucleotide numbers (defined herein) summed up to odd numbers (5/3/1); the simple sums in the deficient dimers are even numbers (4/2). Thus, the preference for odd numbers also appears at the dimeric level. The language of translation (to amino acids in protein) maintains this preference. This, plus the condition for non-overlapping of codon bases, may further restrict the coding language to mostly prime numbers.

Number theory deals with properties of natural numbers. Continuous numbers, real and imaginary, have lost the fundamental properties (odd/even, prime/composite) of numbers. For this reason, number theory is the discrete mathematics least familiar to scientists. Herein, the "quantitative" aspect of numbers is deliberately omitted so as to contrast the "qualitative" mathematics. In addition to the structural, linguistic and musical analogies described by other authors, this disclosure presents a numerical representation/analogy for the genetic code. Numbers are a universal language. Combinatorial uniqueness is the underlying rule for the inter-translation of languages. A combinatorial/number theoretic approach to longer DNA and protein sequences is expected to reveal how the sequences "say it with numbers".

DESCRIPTION OF THE PREFERRED EMBODIMENT

While the invention will be described in connection with a preferred embodiment, it will be understood that it is not intended to limit the invention to that embodiment. On the contrary, it is intended to cover all alternatives, modifications and equivalents as may be included within the spirit and scope of the invention as defined by the appended claims.

METHOD OF NUMERICAL REPRESENTATION OF SEQUENCES

Number theory is directly used to correlate number properties with nucleic acid/amino acid residue properties and sequence properties. The numbers assigned are intrinsic to these residues and sequences.

More specifically (to macromolecular residues/units), the alphabets in the gene and protein sequence languages are uniquely converted to n-numbers and z-numbers, as shown in Table 2. There is a one-to-one correspondence between the (combinatorial) number properties and the coding properties of nucleic acid/amino acid residues.

Three consecutive nucleotide bases form a "codon" in DNA or mRNA, to encode an amino acid residue for the synthesis of protein or give a "stop" signal to terminate the protein synthesis. In the coding region of nucleic acid molecules, the codons are non-overlapping. For example, CTGATT is read as codons CTG and ATT, not as CTG, TGA, GAT, ATT. However, when evaluating the numeric frequencies of base dimers or dinucleotides, overlapping dimers are implied, for instance, CTG is composed of the overlapping dimers CT and TG.

A. The Amino Acid Code

In the translation (the synthesis of protein from the mRNA "editor") process, non-overlapping triplet-base codons are used. The genetic (or amino acid) code is a quaternary code, with quaternary units 0, 1, 2, 3 assigned to the four RNA/DNA bases A, C, U(T), G. There are twelve ways of assigning four units to the four bases, but only one of them is uniquely defined as the n-numbers above and further given below:

$$A=0, C=1, U=2, G=3$$

This definition takes the coding and sequential properties of the units and the bases into account. Base A is zero because non-coding poly-A tail is usually attached to the final mRNA "transcript", thereby making base A a "blank." In three codon positions, the second (middle) position is the most dominant one in determining the coding strategy. The presence of base C in the middle codon position inevitably encodes synonymous quartets. This means C is the most dominant base. In the double-helix structure of the DNA molecule, the pairing A:T involves two hydrogen bonds; the G:C has three hydrogen bonds. In the scientific literature, G and C are the "strong" (S)-bonding bases; A and T are the "weak" (W)-bonding bases. In another classification, A and G are purines (R), C and T are pyrimidines (Y). Numberwise, the S-bases (G/C) take odd numbers, the W-bases (C/T) are even numbers; the R-bases are the extreme numbers (0 and 3) of the quaternary units, the Y-bases take middle numbers (1 and 2). From the above argument, the assignment of n-numbers, as given in Eqn. (2), is unique.

Such a critical choice for the definition of n-numbers derives its origin from the quaternary mathematics of the I Ching, in which the "digrams" and their "ritual numbers" are shown in Table 8:

TABLE 8

Comparison with the Digrams

| Digram | — | — | — | — |
|---|---|---|---|---|
|  | — | — | — | — |
| Name | Old yin | Young yang | Young yin | Old yang |
| Ritual number | 6 | 7 | 8 | 9 |
| Nucleotide Base | A | C | U(T) | G |
| n-number | 0 | 1 | 2 | 3 |

Obviously, n-number=ritual number−6, and yang=odd numbers=S-bases, yin=even numbers=W-bases; "old"=R, "young"=Y. This analogy to the I Ching is 15 discussed in my book *DNA and the I Ching: The Tao of Life* (North Atlantic, Berkeley, Apr. 10, 1991), incorporated herein by reference. Prior to the publication of this book, the analogy and sequential order of 64 genetic codons and the 64 "hexagrams" of the I Ching had also been demonstrated in a 4×4×4 cubic representation (J. F. Yan and S. C. Yan, U.S. Patent No. D313,625, Jan. 8, 1991), incorporated herein by reference.

The coding of amino acids can then be expressed as a Diophantine equation:

$$z=f(i, j, k)$$

where z<64 is the amino acid (AA) number; and i, j, k (=0, 1, 2, 3) are the n-numbers of the first, second, third codon bases, respectively. Coding rules are devised to account for the forms of the Diophantine equation. (Journal of Theoretical Biology, 151: 333–341, Aug. 7, 1991), incorporated herein by reference.

The coding rules have been presented above. They are reiterated as follows.

Coding Rule 1. In order to be information-creative, the function f is equivalent to an operation that transforms n-numbers to z-numbers with z being an odd number, a prime or both. The "Stop" codons take the value 0 (zero), the first odd number (1) and the only even-number prime (2) are also used as z-numbers.

The concept of "creativeness" of information is also derived from the concept of yang. In the most basic binary notation, yang is 1 or odd, yin is 0 or even. For a non-zero information, 1 must present at least once in a stream of binary notation. For example, 000000 gives no information, whereas 000100 and 111111 are non-zero information. The indivisibility property of prime numbers led Euclid to regard primes as "basic units." Thus, the amino acid numbers (z) are the "Euclid units" of life. For the nucleotide bases, the order of "creativeness" is $$C(1)>G(3)>T(2)>A(0)$$

There are two kinds of odd-number primes, the P1 (with the form 4N+1) numbers and the P3 (the 4N+3 form) numbers. 2 is the only P2 number. One of the remarkable properties of P1 numbers is that each P1 number is a unique sum of two squares, one odd and one even. There are eight P1 numbers below 64, equivalent to eight synonymous quartet sets of codons. This leads to the second coding rule.

Coding Rule 2. (The P1 Rule). A P1 number smaller than 64 is a unique sum of squares of one odd number and one even number, each P1 number corresponds to a synonymous quartet (four codons coding one amino acid) specified by the first two codon positions.

The third coding rule relates to R and Y in the third codon position:

Coding Rule 3. (The 4N Rule). Differences in the AA numbers between XZY and XZR are 4N. This rule is violated only when (even) AA numbers 0 and 2 appear in a quartet row of codons.

In a detailed sequential sense, the odd/even, codon positions, and strong/weak bonding are implicitly maintained with binary informational bits. The n-numbers and z-numbers are to be used in the sequential development or coding strategy of DNA and protein sequences.

B. Base Dimers

The shortest base "sequence" is a base dimer. Non-overlapping base trimers are used as codons. In general, whether in the protein-coding regions (exons) or non-coding regions (introns), a base trimer should be considered as composing of two overlapping dimers. An n-mer has (n-1) overlapping dimers, (n-2) trimers, (n-3) tetramers, and so on. There are four kinds of nucleotide bases, four kinds of homodimers (AA, CC, TT, GG) and 12 kinds of heterodimers in DNA.

The frequency of each nucleotide base can be easily calculated from the sequence data. Let the frequency of base 1 be p1, that of base 2 is p2. The frequency of dimer 1 and 2 is denoted by p12. In general, p12 is not equal to the product (p1)×(p2) (which is the frequency of the dimer with random expectation) but $$(p1+r)(p2+r)=p12$$

where r is a correction term. When r>0, the dimer appears in excess and the true dimer frequency (p12) is higher than the random expectation (p1*p2); where r<0 (the deficient dimer) the actual dimer occurs less frequently than random expectation. By extensive compilation of dimer data, the dimer rules are obtained as follows.

Base Dimer Rule 1. In coding and non-coding sequences of DNA and RNA, base dimers with the potential to limit population by frequent mutation are initiated by a pyrimidine (C/T) with a higher order of "creativeness". Dimers with odd number n-sums (CA, CT, TG with n-sums 1, 3, 5, respectively) appear in excess; dimers with even-number n-sums (TA=2, CG=4) are deficient. If appearing in the dominant first two codon positions, dimer TA may form stop codons; CG encodes Arg that may form a mutational "hot spot" in cancer cells.

Base Dimer Rule 2. In eukaryote RNA, dimers initiated by a purine (A/G) and odd-number n-sums, GU (5) and AG (3), are splicing termini of introns (non-coding sequences).

Base Dimer Rule 3. In the RNA world, i.e., before transcription and translation mechanisms were fully developed, there existed strong-bonding poly-GC and weak-bonding poly-AU independently. (Poly-GC Rule): In poly-GC RNA, all dimers and their single-base substitution with W-bases were potentially capable of coding synonymous quartets in the subsequent triplet-base codon world. (Poly-AU Rule): Dimers in the poly-AU and their single-base substitution with S-bases were to code for doublets and singlets.

C. RNA Base Pairing

Watson-Crick pairing in RNA is not as strict as that in DNA. The sum of n-numbers in the pair A:U is 2, that in G:C pair is 4, both "p-sums" are even numbers. In RNA, pairings such as G:U and C:U are also allowed, with odd-number p-sums (5 and 3 respectively). These odd-number p-sums are possible between a codon in mRNA and its anticodon in tRNA, where the pairing occurs in the "wobble" position (third codon position).

Because the ability of base U to form pairs with other bases (except U:U pair), poly-U are usually inserted into an RNA strand to pair up with a segment of poly-GC. This insertion can be very precise (in the number of U's) in the splicing process.

The four p-sums obtained above (2, 3, 4, 5), do not appear as a set of quaternary numbers. They must be redefined by examining the number of hydrogen bonds between base pairs (bp): There are three H-bonds in a G:C pair, two H-bonds in an A:T(U) pair. In addition, in a computer program, R. Staden (Nucleic Acids Res., 1980. 8:817–825) assigned a "score" of one (1) to the G:T pair in tRNA genes.

RNA Base Pairing Rule. From this we define the RNA "pairing numbers" as follows:

| Strong | Weak | Very Weak | Non-pairing |
|---|---|---|---|
| p(G:C) = 3, | p(A:T) = 2, | p(G:T) = 1, | p(other pairs) = 0 |

The pairing numbers are expressed in basic quaternary units.

Example R1. Mitochondrial transfer RNA (tRNA).

Mammal Mitochondrial genes for tRNA compiled by M. Sprinzl et al., (Nucleic Acids Res., 1987, vol. 15 supplement, pp. r53–4179) are used here. From the structure of a typical tRNA, the pairing in four stems are: the longest stem is the aminoacyl stem (A-stem) that has 7 bp, the shortest D-stem has 4 bp. The anticodon stem and T-stem have 5 bp each. Denoting the base pairs as S (strong), W (weak), V (very weak) and N (non-pairs) for pairing numbers 3, 2, 1 and 0, we use the compilation of the tRNA for the codon ATY (Ile) of four species in this example. This yields the following table, where the numbers listed are the base pair counts in each bonding category.

| | Pairing in Mt. Ile tRNA stems | | | | | | | | | | | | | | | |
|---|---|---|---|---|---|---|---|---|---|---|---|---|---|---|---|---|
| | A-stem | | | | D-stem | | | | Anticodon stem | | | | T-stem | | | |
| Species | S | W | V | N | S | W | V | N | S | W | V | N | S | W | V | N |
| Rat | 1 | 6 | 0 | 0 | 1 | 2 | 0 | 1 | 1 | 4 | 0 | 0 | 3 | 2 | 0 | 0 |
| Mouse | 1 | 6 | 0 | 0 | 1 | 2 | 0 | 1 | 1 | 4 | 0 | 0 | 3 | 2 | 0 | 0 |
| Bovine | 1 | 6 | 0 | 0 | 1 | 2 | 0 | 1 | 1 | 4 | 0 | 0 | 3 | 1 | 0 | 1 |
| Human | 1 | 6 | 0 | 0 | 1 | 2 | 0 | 1 | 1 | 4 | 0 | 0 | 3 | 1 | 0 | 1 |
| Consensus | 1 | 6 | 0 | 0 | 1 | 2 | 0 | 1 | 1 | 4 | 0 | 0 | 3 | 2 | 0 | 0 |

The consensus pairing pattern is obtained by the majority of the base pair counts, the underlined numbers are the identical ones among the four species and are considered as being "conserved".

Similar data were tabulated for all 22 tRNA's in these four mammal species. The information for four stems, where each stem furnishes two bits of information (number of S- and W-bonding bp's), results in an octal numbering system. Furthermore, each bit in the octal is mainly concerned with the "degree of conservation" (DC) defined as the number of conserved bits in four stems. The DC values are 0, 1, 2, 3, 4, 5, 6, 7. The Ile tRNA listed above has DC=7.

Example R2. Degree of Conservation (DC) in the genes of mitochondrial tRNA. The following table is obtained from the same compilation by Sprinzl et al. (1987). We also list the z-numbers for the amino acids because each base pairing pattern is specific to a given amino acid.

| Base Pairing and DC of Mammal Mt. tRNA's | | | | | | | | | | |
|---|---|---|---|---|---|---|---|---|---|---|
| | | | A-stem | | D-stem | | Anticodon stem | | T-stem | |
| Codon | A.A. | z | S | W | S | W | S | W | S | W | DC |
| TGR | Trp | 1 | 2 | 5 | 2 | 1 | 3 | 1 | 1 | 3 | 6 |
| ATY | Ile | 2 | 1 | 6 | 1 | 2 | 1 | 4 | 3 | 2 | 7 |
| ATR | Met | 3 | 3 | 3 | 2 | 2 | 4 | 1 | 3 | 0 | 7 |
| ACX | Thr | 5 | 4 | 3 | 1 | 3 | 3 | 2 | 2 | 3 | 0 |
| AAR | Lys | 7 | 3 | 4 | 2 | 2 | 1 | 4 | 2 | 3 | 2 |
| AAY | Asn | 11 | 2 | 5 | 2 | 0 | 1 | 4 | 3 | 2 | 2 |
| CCX | Pro | 13 | 3 | 4 | 0 | 2 | 2 | 3 | 1 | 2 | 2 |
| CTX | Leu | 17 | 1 | 6 | 2 | 2 | 2 | 2 | 2 | 3 | 6 |
| TTR | Leu | 17 | 3 | 4 | 2 | 1 | 1 | 2 | 3 | 2 | 2 |
| CAR | Gln | 19 | 2 | 4 | 2 | 1 | 2 | 3 | 2 | 2 | 2 |
| TCX | Ser | 29 | 0 | 4 | 1 | 2 | 3 | 1 | 3 | 0 | 3 |
| AGY | Ser | 29 | 2 | 5 | 0 | 0 | 1 | 3 | 3 | 2 | 3 |
| GAY | Asp | 31 | 1 | 5 | 1 | 3 | 1 | 4 | 2 | 3 | 1 |
| CGX | Arg | 37 | 2 | 4 | 1 | 3 | 1 | 4 | 1 | 4 | 6 |
| GTX | Val | 41 | 4 | 2 | 2 | 2 | 2 | 2 | 1 | 4 | 4 |
| TAY | Tyr | 43 | 2 | 5 | 2 | 1 | 1 | 4 | 3 | 2 | 5 |
| CAY | His | 47 | 1 | 6 | 1 | 3 | 1 | 4 | 3 | 1 | 3 |
| GCX | Ala | 53 | 3 | 3 | 1 | 2 | 2 | 2 | 2 | 2 | 2 |
| GAR | Glu | 59 | 2 | 3 | 2 | 2 | 1 | 3 | 3 | 0 | 4 |
| GGX | Gly | 61 | 2 | 5 | 1 | 2 | 1 | 4 | 1 | 4 | 0 |
| TTY | Phe | 25 | 2 | 5 | 2 | 2 | 1 | 3 | 3 | 0 | 3 |
| TGY | Cys | 45 | 5 | 1 | 1 | 2 | 1 | 3 | 3 | 1 | 1 |

As before, the DC values are obtained by counting the underlined numerals (the magnitudes of the numbers themselves are immaterial here). When the z-numbers are plotted against DC, it is found that there is a parabolic relationship for seven amino acids: Gly, Ala, His, Val, Leu (CTX), Met and Ile. The least-square values are $$z=58.9-1.155(DC)^2, \quad r^2=0.997$$

where r is the coefficient of correlation, which has an excellent value very close to unity (1). The parabola determined by Gly and Leu (CTX) is simpler in form $$z=61-11(DC)^2/9$$

We note that these seven amino acids are non-aromatic and hydrophobic side chains with a wide range of molecular sizes. Thus, both the z-numbers and the DC values are a measure of conservativeness in the bonding pattern in tRNA stems.

In summary, the nucleotide numbers and the RNA pairing numbers are both basic quaternary units. The n-numbers, correctly defined in this invention, lead to a coding scheme involving mostly prime numbers for amino acids. The four stems in tRNA furnish an 8-bit (octal) information set. The synonymous quartets contain 32 of the total 64 genetic codons. Existing DNA, RNA and protein sequences can be translated into such numbering units to facilitate computation, sequencing and characterization. Through the unique numeric interrelationships revealed by representing DNA, RNA and protein sequences in the manner herein disclosed, previously inapparent characteristics can be discerned and analytic power is greatly enhanced. In the future, 64-bit computer chips can be designed and made as a "biochip" for computation and sequence data processing.

D. Base Oligomer Repeats

In discussing oligomers and polymers of nucleotides and amino acids, it is helpful to recount some standard nomenclatures. For polynucleotide (DNA or RNA) chains, the "head" is also called the 5'-end, the "tail" is the 3'-end. For polypeptides, the head part is the amino or N-terminal, the tail is the acidic or C-terminal. The synthesis of all biopolymers always proceeds from head to tail, on paper the sequence is written from left to right.

Base Oligomer Rule. The primordial cell/soup followed a strategy of repeating base oligomers-tetramers, pentamers, heptamers, etc., but avoiding triplets and multiples of three (trimers, hexamers, nanomers). Trimer boundaries are extrinsic factors created to overcome the uncomfortable occurrence of UA and CG dimers, and to set the stage for triplet-base codons.

Obviously, repeating base monomers leads to homopolypeptides when translated. Base repeats are detected in coding regions, with repeats of the coded oligopeptides. For example, base dimers repeat to form dipeptide repeats:

GCGCGCGCGCGCGCGCGCGCGCGCGCGC . . .
AlaArgAlaArgAlaArgAlaArgAlaArg . . . (First reading frame)
ArgAlaArgAlaArgAlaArgAlaArgAla . . . (Second reading frame)

The third reading frame gives the same order of repeats as the first frame. Thus, poly-Ala-Arg is the only possible product of this sequence.

Example N1. Trimer repeats lead to homopolypeptides.

CTGCTGCTGCTGCTGCTGCTGCTGCTG . . .
LeuLeuLeuLeuLeuLeuLeuLeuLeu . . .
CysCysCysCysCysCysCysCysCysCys . . .
AlaAlaAlaAlaAlaAlaAlaAlaAlaAla . . .

All three frames in this example give homopolymers, albeit of different types.

Repeats of trimers ATG and ATA lead to poly-Met and poly-Ile, respectively, in the universal genetic code. (Both trimer repeats yield poly-Met in mitochondria.) But the second reading frame fails to generate polypeptides because of the stop codons:

```
ATGATGATGATGATGATG ...                      ATAATAATAATAATAATA ...
MetMetMetMetMetMetMet ...    (1st frame)    IleIleIleIleIleIleIle ...
Stop                         (2nd frame)    Stop
AspAspAspAspAspAsp ...       (3rd frame)    AsnAsnAsnAsnAsnAsn ...
```

Example N2. Base Tetramer Repeats. S. Ohno and J. T. Epplen (PNAS, 80 3391–3395, 1983) detected a series of tetramer repeats from a mouse mitochondrial transcript which can be written as

```
TATCTATCTATCTATCTATCTATC ...
TyrLeuSerIleTyrLeuSerIle ...        (1st frame)
IleTyrLeuSerIleTyrLeu ...           (2nd frame)
SerIleTyrLeuSerIleTyr ...           (3rd frame)
```

The order of the repeating tetrapeptide is the same for all three reading frames, although the first residue (underlined Tyr) is shifted one space to the right. The n-sum of the repeat, written as n[TATC]=5, is a prime. The z-sum of the heptapeptide, z[IYLSIYL]=151, is a prime headed by Ile (see P-Examples below for "head" and "center" residues). Within the heptapeptide, z[SI]=31 is a "prime dipeptide".

Example N3. Base pentameric repeats generate pentapeptide repeats:

```
CTGGGCTGGGCTGGGCTGGGCTGGG ...
LeuGlyTrpAlaGlyLeuGlyTrp ...
TrpAlaGlyLeuGlyTrpAlaGly ...
GlyLeuGlyTrpAlaGlyLeuGly ...
```

Although the order of pentapeptide repeats stay the same in three reading frames, the first amino acid (Leu) is shifted two residues to the right for each single-base shift in the reading frame. The n-sum, n[CTGGG]=12, is an even number. The pentapeptide, Z[LGWAG]=193, is a Trp-centered prime.

Example N4. Base Hexamers. Base hexamer repeats do not encode protein. However, there is a non-coding example called "telomere" which is a DNA cap at each end of chromosomes. (R. K. Moyzis, Scientific American, Aug. 1991. pp. 48–55). The human telomere has a repeat of TTAGGG, with n[TTAGGG]=13, a prime.

E. Tripeptides and Oligopeptides

In many aspects, tripeptides are very similar to triplet-base codons when they are both "read" without overlapping. In codons, base G in the first codon always codes for stable amino acids, namely GGX (Gly), GCX (Ala), GTX (Val) and GAX (Asp+Glu). In tripeptides, the collagen proteins are populated with Gly-Y-Z repeats. Gly has the largest z-number and base G has the largest n-number. Thus, the regularity in the exact number of repeats in collagen has its origin from the coding properties of base G. Collagen fibers are constituted by triple helices, with each contact between a pair of helical strands being the Gly residue. The triplex geometry is imposed by the tertiary structure. Another example of tertiary structural constraint is the "leucine zippers" with every heptapeptide headed by Leu. Higher oligopeptide sequence properties can, in turn, be inferred from those of tripeptides.

Tripeptide Rule 1. Tripeptides are constituted by a "head" residue, a middle residue and a "tail" residue. When regularity is present in a protein with triplet or heptad repeats, the head residue is Gly (the largest z-value residue) or Leu (the most abundant residue in nature).

The GenBank data for the frequencies of individual amino acids are those obtained from Release 57, September to November 1988 with 2,268,298 residues. The order in frequencies of occurrence is

L, A, S, G, V, E, T, K, R, I, P, D |0.051| Q, N, F, Y, M, H, C, W

The equal-probability frequency value (1/20 or 0.05) is the one assuming all 20 amino acids have equal chance of appearing in a protein. Note that there are 12 amino acids having higher frequencies than 0.05, while only eight are lower.

Tripeptides are the next hierarchy higher than single amino acids to reach a prime-number z-sum. (Recalling that, except Ile, the z-numbers of the other 19 amino acids are odd numbers). When the z-sum of an oligomer is a prime number, it is called a "prime oligopeptide".

Oligopeptide Rule 1. Prime oligopeptides are found mostly in the highly conserved regions of proteins, in the absence of extrinsic constraints. The head residue of a prime oligopeptide is either Met or Ile, the two smallest n-number amino acids. These two residues are also the initiation residues in an encoded protein.

The "average" z-number of the 19 odd-number amino acids is 29; the average weighted with GenBank frequencies is 44. Therefore, the expected z-sum of a tripeptide lies between 87 and 131. There is a "prime quartet" set of primes (of the form 10n+1, 10n+3, 10n+7, 10n+9) in this range (101,103,107,109). Because of the existence of this set of prime quartet, tripeptides have a high probability to be prime-tripeptides. But this prime rule must be free from the geometrical constraints imposed by the (aqueous) environment. We have found from the general properties of prime numbers, the following mathematical theorem.

F. Theorem 1: the Distribution of Prime Quartets

Prime quartets are defined as prime numbers with the forms 10n+1, 10n+3, 10n+7, and 10n+9. Let X be the number of prime quartets smaller than Y, and let $$X = 2^x \text{ and } Y = 10^y$$

where x, y, X and Y are non-negative integers, then $$30(y-2) = x(x+13) \tag{7}$$

The solutions are x=0, 2, 5, 12, 15, 17, 20 ...
y=2, 3, 5, 12, 16, 19, 24 ...

The cases for x=0, 2, 5 have been verified.

FIG. 1 is a graphical representation of the number of primes in the range of 10n and 10(n+1) wherein said numbers equal P(n). The first three sets of prime quartets are the maxima shown as short horizontal bars in FIG. 1. Specifically, they are 11, 13, 17, 19 (n=1 in FIG. 1)
101, 103, 107, 109 (n=10)
191, 193, 197, 199 (n=19)

For the single amino acids, the most abundant one, Leu is in the first set. The second set provides an "island of stability" for prime tripeptides, the third set for prime heptapeptides.

Tripeptide Rule 2. The non-prime odd-number amino acids, Trp, Phe and Cys prefer the middle or tail residue position in a prime tripeptide or oligopeptide. Trp (z-number=1) is the bulkiest residue, Phe (25) is the largest hydrophobic residue and Cys (45) crosslinks with other cysteine residues to form cystine disulphur bridges.

In analyzing a data bank of proteins, H. A. Saroff (J. Theor. Biol. 115: 191–199, 1985) found 40 tripeptides did not occur in 289,500 residues. Among them are those with two or more Trp, Phe and Cys residues, even though some of them may have prime z-sums as denoted herein with a prime sign (') on the tripeptides: WHC, WTC, FWC', NWC, CVF, CWF', RWF, WWF, CFH, CWH, CWT, HCW, ICW, TCW, WCW', YCW', CDW, MFW', CHW, CIW, WMW', CTW, WVW, EWW', HWW, IWW, LWW', MWW'. However, MCN is a prime tripeptide—with "proper" head Met and center Cys-but was also listed as "no occurrence". This tripeptide does occur (see Example P3, Domain IV below). Apparently, Saroff's data bank is not large enough to draw such a conclusion for "no occurrence" for this tripeptide.

Dipeptide Rule. The dipeptide series IX and XI each has 9/20 chance of being a prime-dipeptide (for X=W, M, T, N, L, S, V, E, C). The frequency values calculated from the equal-probable residues is f(IX)=0.45, and that from the GenBank frequencies g(IX)=0.449. The ratio r=f/g is 1 for prime dipeptides.

Example P1. In the human mitochondrial genome (S. Anderson et al., 1981, *Nature* 290:457–465), there are 3789 residues in the coded proteins. Of these, there are 321 Ile residues; 177 prime-dipeptides IX and 177 prime-dipeptides XI. Therefore, the frequencies g(IX) and g(XI) calculated for this genome are both $^{177}/_{321}$=0.55, which is higher than the value from the GenBank data (0.45). Higher frequencies of prime dipeptides mean intrinsically a higher degree of conservativeness in dipeptides IX and XI. In tripeptides XIZ, the probability that neither XI nor IZ is a prime is (1−0.55)×(1−0.55)=0.20. Thus, the probability that at least one of them is a prime is 1−0.2=0.8 in the human mitochondrial genome.

The frequencies calculated from the data of a 1480-residue transmembrane conductance regulator (TMCR, see J. R. Riordan et al. 1989, *Science* 245:1066–1073) are g(IX)=0.53 and g(XI)=0.47.

Tripeptide Rule 3. (Generalized tripeptide sequence order). Let f(X) denote the probability of a prime tripeptide with at least one residue being X, assuming all 20 amino acids are equally likely to be chosen to form a tripeptide with X; let g(X) denote the probability of a prime tripeptide of at least one X, with the other two residue fractions computed from the GenBank data; and let r denote the ratio f(X)/g(X), then The order for the r values in prime tripeptides is I, M, C, A, V, N, H, T, L, S, E, |r=1|K, F, W, Q, Y, P, D, G, R Higher r values signify the greater tendency to form prime tripeptides, as compared with the random expectation. This is also the order in which the amino acid in question can serve as a "head" residue in the prime oligopeptides.

With the exception of extrinsic (geometrical) constraint that designates Gly and Leu as the head residues, the prime oligomers prefer using Ile and Met as the heads, Gly and Arg as the tails. Structure-wise, Met can even replace Leu in the strict repeats of leucine zippers. Numberwise, Ile has the only even prime, it can behave as a head or a supplementary tail in a prime dipeptide.

The above rules enable one to detect prime peptides from conserved and stable sequences, with strong structural and functional implications.

Example P2. Cysteine switch regions are highly conserved, with prime pentapeptides z[PRCGV]=197 and Z[PRCGN]=167 centered at Cys residue.

Reacting with the cysteine switch is the conserved Zn binding site region AAHELGHS, which can be regarded as two H-centered primes. z[AAHEL]=229 and z[GHS]=137; or as a heptapeptide with a di-histidine sandwich: AHELGHS=313, again a prime. Another di-His sandwich is a prime tetrapeptide Z[HIGH=157, which is the signature of a Rossmann fold (reverse beta turn).

Example P3. In the p53 tumor suppressor gene (M. Hollstein, et al., *Science* 253:49–53, 1991), the prime oligomers in the conserved regions (or the same sequences appearing three times or more) in eight such genes are:

Domain II. Z[MCT]=53, z[M(FCQ)L]=109, z[S(VTCTY)S]=197

Domain II. z[RRCPH]=179

Domain IV. z[MCN]=59, Z[SSCMG]=167, Z[MNRRP]=101, z[IL]=19, z[TI]=z[IT]=7

Domain V. z[(VCA)CP]=197

In the above list, central-C are underlined, the underlined R denotes a mutational "hot spot" probably coded by the base dimer CG. The round parentheses enclose a prime. For example, M(FCQ)L is a prime pentamer in itself, but the trimer FCQ(z=89) is also a prime. The pentapeptide is headed by Met; both the prime trimer and pentamer are C-centered. In the pentamer in Domain V, tripeptide VCA is a prime, which then acts as a single residue to become a "head" trimer, the entire pentamer is centered at the second Cys residue. In Domain IV, TI and IT both appear as prime dipeptides. There is a prime tetrapeptide IRVE (between Domains III and IV) that was not listed as inside the conserved domains, but appeared four times. This tetrapeptide is headed by Ile, with the Arg residue again identified as a hot spot. Also in this region, there is another prime tripeptide FRH centered at a "hot spot" Arg. From these two observations, and from the fact that Arg is coded by synonymous quartet CGX in both nucleus and mitochondrion (but the codons are sparingly used), oligopeptide rule 2 follows:

| X: | W | I | M | T | K | N | P | L | Q | S |
|---|---|---|---|---|---|---|---|---|---|---|
| f(x) | 0.43 | 0.04 | 0.375 | 0.45 | 0.4175 | 0.4525 | 0.41 | 0.4325 | 0.40 | 0.41 |
| g(X) | 0.466 | 0.034 | 0.339 | 0.434 | 0.451 | 0.422 | 0.450 | 0.410 | 0.434 | 0.393 |
| r | 0.922 | 1.19 | 1.11 | 1.07 | 0.927 | 1.07 | 0.911 | 1.05 | 0.922 | 1.04 |

| X: | D | R | V | Y | H | A | E | G | F | C |
|---|---|---|---|---|---|---|---|---|---|---|
| f(X) | 0.3825 | 0.3875 | 0.40 | 0.3725 | 0.395 | 0.40 | 0.395 | 0.36 | 0.4125 | 0.33 |
| g(X) | 0.421 | 0.442 | 0.370 | 0.409 | 0.368 | 0.367 | 0.382 | 0.398 | 0.447 | 0.298 |
| r | 0.909 | 0.877 | 1.08 | 0.911 | 1.07 | 1.09 | 1.03 | 0.905 | 0.924 | 1.11 |

Oligopeptide Rule 2. In addition to Trp, Phe and Cys (three amino acids with odd but non-prime z-numbers) as prime centers, Arg can also serve as an "auxiliary center" which tends to be near the real center. This Arg is also a mutational "hot spot" amino acid coded by codons with stability depressed by CGX (unfavorable base dimer CG as the first two codon bases, see Base Dimer Rule 1.)

Example P3 also demonstrates this rule. The hot spot Arg in Domain III is near the center Cys, the Arg hot spot in Domain IV acts as a center because it is headed by Met. This peculiar property of Arg is not only chemical (Arg is a strongly alkaline amino acid), but more importantly genetical (CG dimer at the DNA level).

Example P4. At the DNA level, the universal genetic code has a hexatet (CGX and AGR) of codons for Arg, but the frequencies of those coded by CGX are less than AGR. In the more symmetrical mitochondrial genetic code, AGR are stop signals, the Arg residue coded by the synonymous quartet CGX also appears infrequently. In fact, in human and bovine mitochondria, the quartet CGX give a frequency of 0.0166 in codon usage. The mitochondria have 60 "sense" codons, each "average" equal-probability codon should give $1/60=0.01666$ in frequency. Similarly, the average codon frequency in the universal code is $1/61=0.0164$. In the 1480-residue TMCR protein (J. R. Riordan et al., cited above), the number of Arg coded by CGX has a fraction of $24/1480=0.0162$, in excellent agreement with the usage in human mitochondria. The fraction of Arg residues coded by AGR in the TMCR protein is $51/1480=0.0344$, which is slightly more than twice as much as that coded by CGX.

The quantities of "frequency per codon" calculated from the GenBank data are listed in the decreasing order as (assuming all GenBank data follow the universal code)

E, K, D, M, Q, N, F, A, I, G, L |0.0164|V, Y, T, W, P, S, H, C,R

Note that both Cys and Arg appear least frequently. These two amino acids are usually flanked by others to form prime centers in conserved regions.

The hexatet codons in the universal and mitochondrial (Mt.) codes have a special trend in the ratio of the frequencies of quartet/doublet running roughly as 0.5, 2, 4, for Arg, Leu, Ser hexatets.

| Genome/gene | A.A. in Hexatet | Frequencies Quartet | Doublet | Quartet/Doublet ratio |
|---|---|---|---|---|
| TMCR | Arg | 0.0162 | 0.0344 | 0.5 |
| Mt. | Arg | 0.0166 | — | — |
| Human Mt. | Leu | 0.1460 | 0.0575 | 2.5 |
| Bovine Mt. | Leu | 0.1242 | 0.0633 | 2 |
| Mouse Mt. | Leu | 0.1165 | 0.0632 | 2 |
| Human Mt. | Ser | 0.0583 | 0.0140 | 4 |
| Bovine Mt. | Ser | 0.0583 | 0.0145 | 4 |
| Mouse Mt. | Ser | 0.0634 | 0.0129 | 5 |

Thus, hexatet codons for Leu are the only set with the normal use of codons. In comparison with their corresponding doublets, for Ser codons, the quartet codons are overused, while the Arg quartet usage is severely depressed, as noted above.

In the synonymous quartets of the hexatet-coded amino acids TCX (Ser), CTX (Leu) and CGX (Arg), the codon usage and preference can be inferred from the base dimer distributions, as follows: Define the first and second bases as the "front" dimer in a codon, the second and third as the "rear" dimer. The third base and the first base of the next codon constitute the "border" dimer. For example, in the sequence ATGACC . . . for the first codon, the front dimer is AT, the rear dimer is TG, and the border is GA. In synonymous quartets, the front dimers alone determine the coding scheme.

In a protein-coding sequence of DNA of length L (with L nucleotide bases), there are (L-1) overlapping dimers. The frequency of the front dimer CT is simply $$f(CTX) = \text{No. of CT as front dimers}/(L/3)$$

The frequency is "normalized" in such a way that the maximum number of front dimers is the number of the encoded amino acid residues (U3). The frequencies f(TC) and f(CG) are defined similarly. The frequencies of the bases are simply the fractions f(a), f(C), f(T) and f(G) in the L bases. Thus, the frequency ratio may be expressed as:

$$r(CTX) = f(CTX)/[f(c) \times f(T)].$$

That is, the ratio of the observed front dimer frequency to the product of its monomeric random frequencies. Higher r values mean a stronger preference for the dimer to be at the "front."

Rule of Quartets S=L×R. The frequency ratios for the quartet codons TCX (S), CTX (L) and CGX (R) are interrelated by $$r(TCX) = r(CTX) \times r(CGX)$$

The entire coding regions of three mitochondrial genomes are found to obey this rule, so are two genes in the human mitochondrion (Cytochrome b and U.R.F. 3 in the data of Anderson et al., 1980. *Nature* 290:457–465). The only non-mitochondrial gene obeying this rule is the recently cloned NMDA receptor gene in rat brain (K. Moriyoshi et al., 1991, *Nature* 354:31–37). The following table verifies this rule.

| | Entire coding Mt. genomes | | | | | |
|---|---|---|---|---|---|---|
| | Human | Bovine | Mouse | Cyt.b | U.R.F.3 | NMDAR |
| Length (L) | 11367 | 11373 | 11435 | 1140 | 345 | 2814 |
| r(CGX)-ARG | 0.40 | 0.47 | 0.55 | 0.45 | 0.27 | 0.61 |
| r(CTX)-Leu | 1.75 | 1.62 | 1.54 | 1.68 | 1.76 | 1.37 |
| R(CGX) × r(CTX) | 0.70 | 0.76 | 0.85 | 0.75 | 0.48 | 0.84 |
| r(TCS)-Ser | 0.70 | 0.76 | 0.84 | 0.76 | 0.49 | 0.83 |

Example P5. Phe-Centered primes. Because of the z-number of Phe is non-prime (25), Phe may also serve as a prime center. One example is the very ancient conserved segment appearing in the development genes of fly, mouse, C. elegans etc. which is a prime 10-mer (C. Kenyon and B. Wang, 1991, *Science* 253:516–517):

z[K((IW)FQ)NRRMK]=149 where F acts as a center for the prime tetramer IWFQ, with z[IW]=3, z[IWEQ]=47. All the z-sums are prime numbers.

Example P6. Another example F-centered is the famous cystic fibrosis gene (J. R. Riordan et al., 1989, cited above.) The omission of a Phe residue at residue No. 508 was found in 70% of mutations in cystic fibrosis patients. The amino acid sequence three Ile residues upstream from F(508) is

. . . IKENIIFGVSYDEYRYR . . .

Although the conserved regions are not identified, we can still deduce from the rules given above and notice that z[IKEN]=79, z[IIF]=29, z[IIFGV]=131

After deletion of the center Phe, the second prime is a 9-mer:

z[IIGVSYDEY]=311 which no longer has a stable center. A higher prime oligomer has less chance of being conserved. Therefore, the deletion of F(508) causes instability in the chain so severe to the function of the protein.

Example P7. Two Ile residues supplement Phe to form a prime tripeptide IIF, as given in the last example. Likewise, one Ile gives Cys a prime dipeptide: IC or CI.

These data were taken from the compilation of bound (as S-S disulphur) and unbound (in S-H state) Cys-centered sequences by S. M. Muskal et al. (Prot. Eng., 1990, 3:667–672):

In 270 S-H sequences there are 9 IC and 15 CI dipeptides.

In 403 S-S sequences there are 17 IC and 5 CI dipeptides. As stated before (Oligomer Rule 1), Ile may serve as a head and a "supplemental" residue to a prime dipeptide. As a head residue Ile leads a peptide chain without being constrained by geometrical factors. This means IC is an inherently "free" dipeptide. The fact that IC>CI in the S-S state of Cys-centered sequences in turn suggests that the "bound" S-S is freer than the "unbound" S-H state. This statement is also reflected by CI>IC in the S-H cysteines. It may sound surprising that a "bound" cysteine is freer that an "unbound" one. But in terms of the flanking sequences, a free, unhindered S-H bond in cysteine should have a higher chance of forming disulphur bridges with other S-H bonds.

Example P8. Continuing the line of the bound (in S-S state) cysteines, we extract from the same compilation of data, the following: divide the C-centered prime peptides into two groups, "Long" and "Short". The long primes are defined as heptapeptides and higher oligomers (including those which never reach a prime z-sum in sequences listed up to 15 residues). The short ones are hexamers and lower. A total of 187 pairs of bound cysteines are obtained. This compilation gives specific Cys residues that are mutually bound. Of the total primes, 63.63% are small primes, and 36.36% are large primes. The actual number of the Long-Long pairs is 29, corresponding to an actual fraction of $29/187=0.155$. This actual fraction can be compared with the random expectation of 0.3636×0.3636 or 0.1322, the result is $0.155/0.1322=1.17>1$ which means that is an excess of Long-Long pairs of prime peptides. Similarly, the Short-Short pairs have an actual fraction of $80/187$ or 0.4278, which on dividing by 0.4048(0.6363×0.6363) yields 1.06. Thus, there is a slight excess of Short-Short pairs. The actual fraction of Long-Short and Short-Long pairs is $78/187=0.4171$. The random expectation is 2×0.6363×0.3636=0.4627. The ratio 0.4171/0.4627=0.902<1 means deficient Long-Short pairs.

Thus, disulphur bridge formation is favored when the crosslinking C-centered prime peptides are of comparable lengths or types, e.g., Long-Long and Short-Short.

Example P9. Heptapeptide sequences with coiled coil structure (A. Lupas et al., 1991, *Science* 252:1162–1164). In this particular conformation (coiled coil), the alkaline residues (K, R, Q, N) are found (by statistical analysis) to prefer the tail part of the heptapeptides. Residues acting as heads are L, I, M, V, A. The central (fourth) residue position is populated by L, A, Y, M. That I, M residues appear as the heads does not come as a surprise. But that L and M appear as both head and middle residues may indicate a leucine zipper type of growth strategy.

| EBP          | LTS   | DNDL | (LRK) | R | VEQ   | LSR   | ELDT | LRGIFRQ    |
| ------------ | ----- | ---- | ----- | - | ----- | ----- | ---- | ---------- |
| Mouse C-myc  | LTS   | EKDL | (LRK) | R | REQ   | LKH   | KLEQ | LRNSGA     |
| Hman N-myc   | (LQA) | EEHQ | LLL   | E | (KEK) | (LQA) | RQQQ | LLKKIEH    |
| HUMAN L-MYC  | (LVG) | AEKR | MAT   | E | KRQ   | LRC   | RQQQ | LQKRIAY    |
| v-jun        | LEE   | KVKT | LKA   | Q | NSE   | LAS   | TANM | LREQVAQ    |
| v-fos        | (LQA) | ETDQ | LED   | K | KSA   | LQT   | EIAN | (LLK)E(KEK)|
| GCN4         | LED   | KVEE | LLS   | K | NYH   | LEN   | EVAR | (LKK)(LVG)E|
| EmBP-1       | LAP   | GRAA | LTS   | A | APN   | LNI   | GRDP | LSASPSS    |
|              | LVQ   | GEVN | LAQ   | K | VSE   | LTA   | ANGT | LRSELDQ    |
|              | (LKK) | DCKT | MET   | E | NKQ   | LMG   | KILS |            |

The conserved prime tripeptides are underlined. Being "conserved" means those which appear twice or more in these limited data. There are three conserved non-prime tripeptides: LTS, REQ and QQQ. The preferred centers C and F each appears only once, but both with a proper head (I or L—in leucine zippers). The prime heptapeptide z[LRCRQQQ]=193 is C-centered (human L-myc). The prime tetrapeptide z[IERQ]=83 is F-centered. There is no Trp in the above sequences.

Example P11. As noted before, collagen peptides are repeats of the type Gly-X-Z. (They will be called the Gly-3 repeats.) Such repeats do not obey prime oligomer rules. In the clb-2 in C. elegans-2 collagen (Guo et al., 1991, *Nature* 349:707–709), the preference of a residue to the second or third position is asymmetrical. For example, if the dipeptide XG>GX, obviously the residue X prefers the third position. The number of appearances of such residues are shown in parentheses:

XG>>GX(at least five times as frequent)—

PG(215)>GP(39)

CG(7)>GC(1)

GX>>XG (5 times—or more—as frequent, second residue position strongly favored by X)—
GL(81)>LG(4)
GM(18)>MG(2)
GI(15)>IG(2)
GY(47)>YG(4)
GF(19)>FG(3) Thus, the most abundant tripeptide is GLP. The usual head residues (M and I) are "suppressed" by the strongly geometrical constraint of a Gly head in collagen proteins. The head of the leucine zipper, the Leu residue, is also suppressed. The usual centers F and its structural analog Y, remain as centers (second position of G-3 repeats). However, Cys prefers the tail (third) position in the repeating tripeptides.

Example P12. Silk-moth chorion protein sequences compiled by S. J. Hamodrakas et al., (Protein Eng., 2:201–207, 1988). They seem to be mixtures of L-14 and G-6 repeats (twice the sizes of leucine zipper and collagen repeats).

| B e2G12 | B m2807 | B m1768 | B Hc-B12 | B pc401 | C pc404-H12 |
|---|---|---|---|---|---|
| LGVA | LGIA | LGIA | LSIC | LGVA | LSVT |
| SENSYE | SENRYE | SENRYE | SENRYK | SENMYE | SENTIE |
| GTVGVC | GTVGVC | GTVGVS | GDVCVC | GCVGVA | GWAVT |
| GNLPLL | GNLPFL | GNLPFL | GEVPFL | GNLPFL | GQLPFL |
| GTAIVT | GTADVA | GTADVA | GTADVC | GTAGVE | GAVVTD |
| GEFSTG | GEFPTA | GEFPTA | GNMCSS | GVFPTA | GIFPTV |
| GLGGIN | GIGEID | GIGEID | GCGCID | GAGVIN | GAGDVW |

The sequences are shown in a helical form, as indicated in the first sequence. The first line is read from left to right, the second line from right to left, and so on. The 15-mer repeating Leu and 6-mer repeating Gly are underlined. In each sequence, five G-6 repeats are joined in a tail-to-tail and head-to-head fashion. Prime oligomers appearing twice or more are:

z[IAEY]=157, z[EI]=61 and z[IN]=13 are sequences involving Ile—as head residue or supplementary residue.

z[EFP]=97 AND z[VCL]=103 are F- and C-centered primes.

Figure 2:
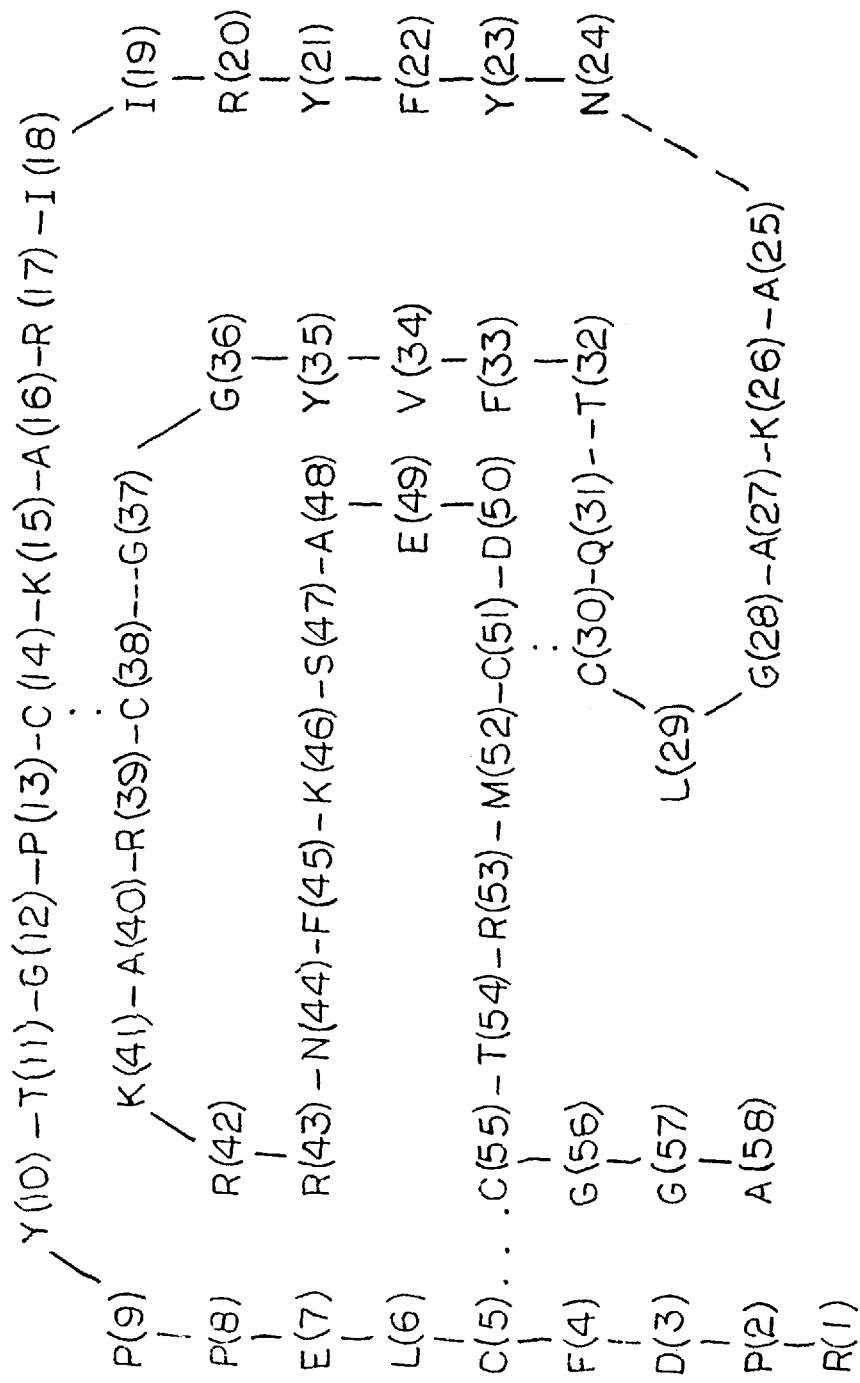
FIG. 2 is a diagrammatic representation of protein folding in bovine pancreatic trypsin inhibitor.

Example P13. Protein Folding. The folding of bovine pancreatic trypsin inhibitor (BPTI) is a classic protein folding problem that has been intensively studied (T. E. Creighton, 1974 J. Mol. Biol. 87: 603. J. S. Weissman and P. S. Kim, 1991, *Science* 253:1386–1393.) FIG. 2 is a representation of protein folding in bovine pancreatic trypsin inhibitor.

This protein is only 58 residues in length, with six cysteine residues forming three disulphur bridges. Its primary structure (sequence) is taken from Creighton's paper (the cystine bridges are shown as dots) as shown in diagram 4, (using the rules at hand, we first detect from the sequence the following):

(a) Primes headed by Ile or Met.

$$z[I\!I\!RYF\underline{Y}N] = 163, \text{ with } z[I\!I\!R] = 41, z[I\!I\!RYF] = 109$$
$$22$$

$$z[MRT\underline{C}G] = 151$$
$$55$$

The probable centers are underlined and numbered. The primes headed by Ile do not involve Cys and will not be of concern.

(b) C-Centers and F-Centers.
Two C-centered pentamers are $$GP\underline{C}LA \text{ and } GG\underline{C}RA$$
$$\overline{14} \quad \overline{38}$$

The tripeptide z[DFC]=71 is a prime with an F-center, otherwise, there is no prime around C(5).

(c) Overlapped primes.
The tripeptide $$z[D\underline{C}M] = 79$$
$$51$$

is a prime. However, M(52) has been used in (a) as a head residue, so that the Met in trimer DCM is an overlapped residue which is no longer a head. If Met is discounted as being used, then there is no prime around C(51). Likewise, the heptapetide $$z[CQT\underline{F}VYG] = 239 \text{ with } z[TFV] = 71$$
$$33$$

both can be considered as F-centered. The last residue G(36) has been used in (b) for the pentamer GGCRA so that G(36) is an overlapped residue. If overlapping is disallowed, then there is no prime around C(30).

In Example P8, we applied the prime rules to strictly C-centered sequences and concluded the principle of "like crosslinks like": Long with Long and Short with Short primes. In Example P13, the classification is more elaborate, the order of discussion is (a), (b), (c) with decreasing importance. The pair C(14)-C(38) is a pair of prime pentamers. The pair (5-55) is a crosslinking of Short-Short primes. This leaves us with a non-prime pair (30-51). These three disulphur bridges are also the set found as the native S-S bonds.

The disulphur bridges are the most important factor in the problem of protein folding, which in turn is the main structural feature in the catalytic activity of proteins and extremely useful in drug design. This example is the first instance to determine crosslinks from the information on the primary structure (sequence).

SEQUENCE ANALYSIS BY BUMBERS: PROTEINS

As a number code to the protein sequence language, the amino acid numbers (z) derived previously (1, 25, 45 and seventeen prime numbers smaller than 64) are used to characterize oligopeptide motifs. The grammatical rule of this language is expressed with two theorems governing the collective properties of oligopeptides. This numeric representation contrasts particular sequence patterns. The language's equivalent forms range from simple repeating phrases (like in baby talk) to elegant and sophisticated seven-word poems (like those of Li Bai). Sequence examples are given for frequently occurring repeats in silk fibroin, collagen triplet repeats and mutational hotspots, ancient ferredoxin, coiled coil and leucine zipper patterns, runs of amino acids, protein "huntingtin," hydrophobic transmembrane helices, implicit heptad repeats in amyloid protein, etc. A heptad scan method is applied to prion proteins that form amyloid through hydrogen bond zippers.

I. Introduction

Fibrous proteins such as silk threads are marvellous natural bipolymers with strength unmatched by synthetic ones. Spider silk has a tensile strength greater than steel. Silk fibroin and collagen proteins have distinctive dipeptide and tripeptide repeats as shown in their DNA and amino acid sequences. However, the frequency and pattern of these oligopeptides and repeats have never been rationalized satisfactorily. A simple but radically different approach to these puzzles is offered here. The sequential and structural features demonstrated will help clarify various problems in drug design and protein engineering.

A basic language in polymers is the enumeration of their structural units as degrees of polymerization (DP). An amino acid sequence in proteins or polypeptides (the primary structure) is defined by the series (i,z), where i=1 to DP is the "residue number" and z is a characteristic letter in the 20-letter protein language as those used and deposited in large databanks. Even for a sequence as short as heptapeptide, there are $1.28 \times 10^9$ possible "words" that can be formed with these 20 letters. This number is much larger than all the encoded heptapeptides that can be accomodated for by the entire human genome.

In languages, grammatical rules are ways to drastically reduce such huge numbers to a manageable size. For the 4-letter DNA language, Ohno (Proc. Natl. Acad. Sci., USA, 85: 9630–9634, 1988) has deduced the dinucleotide usage rule of "TG/CT/CA-excess and CG/TA-deficiency". With this rule, Ohno and his co-workers were able to explain the abundance of the trinucleotide CTG and its complementary CAG, and the pairing of pre-tRNA and complementary anticodons (Ohno, 1988; Rodin et al., Proc. Natl. Acad. Sci., USA, 90: 4723–4727, 1993). A grammatical rule for the protein language is also needed, and is provided herein.

One way of translating the primary structure to the secondary and higher-level structures in proteins is converting the characteristic parameter z into numbers so as to facilitate calculation for predictive purposes. Conformational parameters such as those of Chou and Fasman (Annu. Rev. Biochem., 47: 251–276, 1978) come to mind as such a representative approach. However, these numbers are not unique in that two amino acids can even share a single value of, say, a helical parameter. Furthermore, conformational parameters say nothing about the abundance and compatibility of dipeptides and tripeptides, the specific patterns of higher oligopeptides, nor about the coding "history" from DNA sequences. Here, a new set of numbers, unique but universal, is provided to contrast such properties and patterns of oligopeptides.

Natural numbers are the natural choice for z. Because protein sequences are translated from the coding DNA and RNA sequences, the "amino acid number" z should be chosen from natural numbers below 64. The nucleotide bases must first be converted to quaternary units 0, 1, 2, 3. There are 4!=24 ways of assigning four numbers to the four bases. But there are $64!/(64-20)!=4.77 \times 10^{34}$ ways of choosing twenty numbers, out of a total of 64, for the twenty amino acids. Such an astronomical number precludes any arbitrary assignment for the z-numbers. Fortunately, coding combinatorics based on the genetic code nicely deduce a "one-to-one correspondence" between coding properties and number properties for a unique set of numbers (Yan et al., 1991). This set of z-numbers appears in Table 2 above, together with the three-letter and single-letter notations of amino acids.

II. The Approach

The approach adopted is a novel one that may be the first direct application of number theory in "bioinformatics."

Derived from the coding scheme, the z-numbers are "intrinsic" enough so that their simple sums may "extrinsically" reflect collective properties for oligopeptides. Taking simple linear combinations is a practice commonly used in chemistry, e.g., molecular mass is the sum of atomic masses; molecular orbitals are sums of atomic orbitals. By so doing the z-sum of tripeptide GAP, written as z (GAP)=61+53+ 13=127, is a prime number and GAP is called a "prime tripeptide". The z-sums of oligopeptides still retain basic number properties: odd/even, prime/nonprime (Yan et al., 1991). In this way, the number code used for protein sequences is a computable language.

As one group or several groups, the z-numbers in Table 2 have the following properties: (i) All except the three underlined are prime numbers. Amino acids coded by synonymous codons take prime numbers of the form 4k+1. (ii) For all alkyl side-chain amino acids except for Ile, the magnitude of z-numbers increases with decreasing molecular masses. (iii) Ile and Met take the first (and only) even prime and the first odd prime numbers, respectively, contrasting the use of these two "initiation" amino acids in protein synthesis. (iv) According to a theory on the evolution of the genetic code in an "RNA world", peptides could have been synthesized in "clefts" formed by RNA bases (Mellersh, Origin of Life & Evol. Biosphere, 23: 261–274, 1993). For synonymous quartet codons except those coding for Gly and Arg, the angle B between the first two bases (Mellersh, 1993) is related to the z-numbers by $$z=64\cos^2(B/2)$$

which holds for ten amino acids, with Ile and Val—the two α-branched amino acid side-chains—showing the largest deviations.

Properties of z-sums and the abundance and patterns of their representative oligopeptides are the main focus of the interpretive scheme herein described.

III. Prime Tripeptides

In Table 2 above, seventeen amino acids have prime z-numbers. Of the three nonprimes, Trp and Cys are the least abundant in nature. The probability of finding a "prime amino acid" at random is at least $17/20=0.85$. A calculation with z-numbers in Table 2 shows that 3061 out of the 8000 possible tripeptides are "prime tripeptides". Thus the probability of finding a prime tripeptide at random is $3061/8000= 0.38$. Calculation with 3,200,000 iterations gives the probability of finding a "prime pentapeptide" at random as 0.30. These calculations are based on the assumption that all the 20 amino acids have equal chance of being chosen at random.

At this juncture it is better to illustrate the theoretical argument with a model protein: The α1 chain of Type I human collagen (Nemethy & Scheraga, Biopolymers, 21: 1535–1555, 1982; Bernard et al., Biochemistry 22: 5213–5226, 1983; Kuivaniemi et al., Biochem. J., 252: 633–641, 1988; Kuivaniemi et al., FASEB J. 5: 2052–2062, 1991; Tromp et al., Biochem. J. 253: 919–922, 1988) has an uninterrupted chain of 338 triplet repeats of GXZ, where X and Z can be any amino acid. A theoretical calculation similar to the above examples shows that, of the 400 possible GXZ triplets, 144 are prime, making a probability of finding a prime GXZ as $144/400=0.36$. The observed number of prime GXZ in α1(I) is 143, or a prime fraction of $143/338=0.42$. The ratio $0.42/0.36=1.16$ shows that there is a greater chance of finding a prime GXZ than what can be randomly expected. (To reiterate, unless otherwise specified prime oligopeptides are written in capital letters and nonprimes in lowercase, e.g., GAP is prime and gpp is nonprime.)

Dolz and Herdemann (Biopolymers 25:1069–1077,1986) also analyzed tripeptide distribution in Type I collagen. Somewhat arbitrarily, they defined "typical" tripeptides as being gpp, GPA, GAP, gep, GAR, GER and gpk. These "typicals" are found to cluster around each other. For example, tripeptide GAR is enriched in the neighborhood of the "typicals" whereas gak is deficient. In the language of prime trimers (tripeptides), however, this can be attributed to the fact that GAR (z=151) is a prime but gak (z=121) is not.

The general form GEX yields a prime z-sum when X=K, N, L, Q, S, D, R, Y, H, A, E, G—twelve amino acids out of a total twenty. Thus the "prime propensity" (pp) of dipeptide GE, written as pp(GE), is $^{12}/_{20}$ or 0.6, which is a probability measure obtained by assuming all twenty amino acids have equal chance of forming trimers with GE. The actual fractions of GEX primes calculated from sequence data of Caenorhabditis elegans and human Type IV collagen (Guo et al., Nature 349:707–709, 1991) are even higher, 0.745 and 0.617, respectively. This and the above examples prove a frequent occurrence of prime trimers. Frequency comparison is better made for a pair of tripeptides with similar chemical properties or a group of tripeptides with a similar environment. This theme of property comparison will arise from time to time in this paper. Suffice it to say at this point that prime peptides may be present in a higher frequency than their nonprime analogs.

Returning to the theoretical treatment, two prime numbers that differ by 2 are a pair of "prime twins" (Rosen, "Elementary Number Theory and Its Applications," 3rd Ed. p. 69, Addison-Wesley, Reading Mass., 1993), e.g., 11 and 13; 17 and 19. Four consecutive prime numbers in a decade in the forms 10n+1, 10n+3, 10n+7, 10n+9 are a set of "prime quartets." The maximum prime density in a decade of numbers is a set of prime quartets. The first set, with n =1, or with prime numbers 11, 13, 17, 19, are the z-numbers for the abundant amino acids Asn, Pro, Leu, Gln, respectively. An "average" amino acid number lies between 29 and 35, as evaluated from Table 2. Thus, the second set of prime quartets, with n=10, or prime numbers 101, 103, 107, 109, are most likely the sums for three consecutive amino acids (a tripeptide). The third set, for prime numbers 191, 193, 197, 199, encompasses the range for seven amino acids (heptapeptides).

Indeed, repeating patterns of tripeptides and heptapeptides appear frequently as easily recognizable motifs in proteins. Collagen GXZ tripeptides and leucine zipper heptapeptides are well-known examples. To describe the prime quartet distribution, a general theorem has been deduced that holds for numbers up to 100,000, as previously described.

Theorem 1: the Distribution of Prime Quartets. Let X be the number of prime quartet sets smaller than Y and let X and Y be expressed in binary and decimal forms, respectively:

$$X=2^x \text{ and } y=10^Y$$

where x, y, X and Y are non-negative integers. There is a relationship between x and y:

$$30(y-2)=x(x+13)$$

The solutions are
x=0, 2, 5, 12, 15, 17, 20, . . .
y=2, 3, 5, 12, 16, 19, 24, . . .
The cases for x=0, 2, 5 have been verified with a prime number table (Beryer, CRC Standard Math, Tables 27th Ed. pp. 84–91, CRC Press, Boca Baton, Fla. 1984) up to 100,000. This theorem states that, below $10^5$ there are $2^5$=32 prime quartet sets with n=1, 10, 19, 82, 148, 187, 208, 325, 346, 565, 943, 1300, 1564, 1573, 1606, 1804, 1891, 2227, 3172, 3484, 4378, 5134, 5533, 6298, 6721, 6949, 7222, 8104, 8272, 8881, 9784, 9913.

IV. Prime Propensity

The concept of prime propensity, introduced for pp(GE) above, can be applied to any even number. Calculation with z-numbers in Table 2 immediately reveals a pattern that, when the even number is divisible by 6, the prime propensity reaches a local maximum. This property is very important for dipeptides and hexapeptides, because it is a measure of the propensity or probability of reaching a prime tripeptide or heptapeptide on acquiring one more amino acid. Since z (GE)=120 and 120 is divisible by 6, thus pp(GE)=pp(120) =0.6 which is a high probability. A high prime propensity of a dipeptide also means that its constituent amino acids are mutually compatible and the dipeptide itself may appear frequently in a protein.

Theorem 2: Maximum Prime Propensities. The prime propensity of an even number m, pp(m), is a local maximum when m is divisible by 6. In particular, the absolute maximum is pp(0)=0.85 (for "monomers"); for oligomers, the three largest prime propensities are pp(6)=pp(12)=pp(42)= 0.65.

Expressing all even numbers in three forms, 6k, 6k+2, 6k+4, this theorem says that pp(6k) is greater than the pp of the other two forms, in the neighborhood of 6k. This theorem can also be proven with Theorem 1 by noting that the differences between adjacent prime quartet sets listed under Theorem 1, or 10Δn, have a largest common factor of 30, which contains a factor of 6.

In terms of the divisibility by 6, the amino acid numbers in Table 2 can be classified as Type 6k+1: W, K, P, Q, F, D, R, Y, G Type 6k−1: T, N, L, S, V, H, A, E In addition, there are Type 6k+2, which has only Ile, and Type 6k+3, which has only Met and Cys. In forming "6k-dipeptides", Type 6k+1 and Type 6k−1 amino acids are mutually compatible. Amino acids Ile, Met and Cys are "incompatible" with the other 17 amino acids listed above. This incompatibility may break a repeating pattern. For example, human Type IV collagen has 429 triplets (Guo et al., 1991), and in 41 interruptions or gaps between GXZ triplets, 20 gaps are found to contain Ile, Met or Cys. However, Ile and Met are known to be the "initiation" amino acids in protein synthesis, and both also serve as "starters" to hydrophobic helical heptads (see Section XIII below).

The dipeptide compatibility can be found in the repeats $(GA)_n$ and $(GS)_n$ in silk fibroin (Mita et al., J. Mol. Biol. 203: 917–925, 1988) and $(PE)_n$ in E. coli iron-binding protein. These simple repeats are much like baby-talk speech: "Ma-Ma" and "Pa-Pa." The ancient ferredoxin repeats (Eck & Dayhoff, Science 152: 363–366, 1966)

ADSGAPSG ADSGAPSG ADSGAPSG . . .

−+−+−+−+ −+−+−+−+ −+−+−+−+ . . .

are also an example of this "nearest neighbor compatibility." The dipeptide compatibility symbols (+) and (−) written under the sequence are used to denote the 6k+1 and 6k−1 types, respectively.

Heterodipeptides formed with prime twin z-numbers are 6k dipeptides and are present frequently in proteins; e.g., NP, LQ, DS and GE (see discussion on GEX primes above) are such abundant dipeptides. Prime dipeptides can be formed with one Ile residue, e.g., IN, IL, IS and IE, all of them abundant. Among homodipeptides, only z (MM)=6 and z (CC)=90 are divisible by 6. Indeed, the observed CC frequency is almost twice that which can be expected randomly in any protein; and MM can be detected in the "runs" of Met (see below).

The above two theorems have explained the seemingly unsolved puzzle of dipeptide and tripeptide repeats, with more examples to be given below. These two theorems constitute the basic grammatical rule in the 20-letter protein language, once the 20 letters are translated into their z-numbers in Table 2. Any arbitrary assignment of numbers other than those specified in Table 2 will certainly fail to generate and obey such elegant theorems.

V. Patterns Derived From Collagen Triplets

In human Type I collagen al chain (FIG. 3), the most abundant tripeptide of the form GXZ is gpp, the next being gep. Both are nonprimes. On examining the context surrounding these tripeptides, it is noted that in most cases gep is preceded by a Lys residue, making it a prime KGE. The chemically analogous kgd appears much less frequently. This frequency difference is written as KGE>kgd. Much like the result GAR>gak noted above, the fact that "prime>nonprime" for structurally analogous sequences in the same protein lends more credence to this approach.

"Reading" the tripeptide as KGE instead of gep means that the "reading frame" need not be confined to the form of GXZ, and that a "frameshift" is allowable. FIG. 3 actually depicts the collagen triplets in three forms: GXZ, ZGX and XZG, and capital letters are used for the residues that head a prime trimer. Type I collagen has an uninterrupted strand of 338 GXZ repeats, with 143 prime tripeptides in the form GXZ, 143 prime tripeptides in the form XZG, and 144 primes in the form ZGX. The entire chain has (1014-2) overlapping trimers. The prime fraction is therefore (143× 2+144)/(1014-2)=0.425, which is slightly larger than that calculated for the case of non-overlapping tripeptides.

The same enumeration can be performed for the Cys-centered trimers that appear frequently in gaps between GXZ repeats in Type IV collagen from C. elegans. As noted before, Cys residues can break repeating patterns. Prime trimer DCG is present more frequently than the structurally similar ecg, i.e., DCG>ecg. Applying the "frameshift" technique twice toward the left of the nonprime but abundant gpp, frequently the prime pentamer PPGPP is reached. In fact, three overlapping PPGPP pentamers are located at the C-terminus to nucleate the "zipping" of three Type I collagen chains—two α1 chains and one α2 chain (Kuivaniemi et al., 1988; Kuivaniemi et al., 1991; Tromp et al., 1988).

Abundant GXP tripeptides are primes only when X=T, S, A; that is, pp(GP)=3/20=0.15, which is not a high fraction. This means that in the GXP primes, the G_P serves as a "template" for small residues Thr, Ser and Ala. Similarly, abundant "sandwich" pentamer PGXPG is a prime if X=Q, W, F, Y; that is, PG_PG is a template for Gln and aromatic side-chain residues. Extending further to another sandwich form, XPGXPGX is a prime heptamer if X is a hydrophobic (aliphatic and aromatic) amino acid. This is a natural pattern for coiled coil heptamers, with hydrophobic residues at positions 1 and 4 of the heptad.

Examples of this coiled coil pattern are abundant in human collagens: For Type I collagen, there are five prime peptides (in capital letters) and one nonprime (lowercase): IAGAPGFP, LPGAKGL, APGLQGM, ATGFPGA, APGAPGA; akganga. In Type IV collagen (Guo et al., 1991), there are six prime heptamers and octamers, and three nonprimes: LPGLQGV, LPGLKGL, LKGLQGL, LPGIDGVK, LPGLQGIK, LPGLPGIP; lpgldgip, ipgfdgap, aqglpgit; plus two prime heptamers with charged residues at position 7: IGEIGEK, APGLPGE. Only APGAPGA in Type I collagen remains in a "sandwich" form. Type I has mostly A7 (heptamer headed by Ala) primes, while Type IV has exclusively L7 or L8 primes. Collagens are such model sequences that they can yield a wealth of information on the patterns of frequently occurring motifs. The above examples demonstrate the detection of prime tripeptides, pentapeptides and heptapeptides, with pattern implication for non-collagen sequences.

VI. Mutation in Type I Collagen

In Type I collagen, three chains coil around each other to form a triple helix, which is "nucleated" from the "C-terminus" of the chains. The triple helix then propagates with a zipper-like mechanism toward the "N-terminus" (Byers, Trend Gen. 6: 293–300, 1990). In human patients with an inheritable brittle bone disease called osteogenesis imperfecta (OI), some of the repeating glycine residues mutate by a single-base substitution in their DNA. FIG. 3 shows these "point mutations" with their third codon bases (above the mutated glycine, inside parentheses) and the mutant amino acid residues (under the mutated Gly) . The mutant residues are written in capital letters if the OI disease is severe; and in lowercase letters if the disease is mild.

The mutant glycine residues are likely to be located within a prime peptide. Thus, in the two chains of Type I human collagen, the frequently occuring prime pentapeptide PPGPP occurs 7 times, (here underlined is the mutant glycine). Various combinations of prime AGP occur 12 times, mostly in the α1 chain. Combinations of prime SGP occur 5 times, mostly in the α2 chain (not shown in FIG. 1). The glycine bonds (denoted by a short bar) cleavable by mammalian collagenases (Fields, J. Theor. Biol., 153: 585–603, 1991) are also found to be at or near the end of prime oligomers: PGPQG- and PGPLG-I. Both prime peptides have identical z-sums of 167.

In the four prime peptides illustrated earlier—GAR, KGE, DCG and PPGPP—three are discovered by shifting the reading frame. These patterns share a common feature of having a "cardinal" residue in the central position. These chemically active cardinal residues generally have large z-numbers (G,E,A) or nonprime z-numbers (such as Cys). This property enables one to detect mutations in consecutive glycine residues in Type I collagen: By scanning through the three reading frames, if a prime pentapeptide contains three overlapping prime tripeptides, it is called a "perfect" prime pentapeptide with two active, mutable glycine residues. Indeed, in human Type I collagen al chain (FIG. 3), there are three such perfect primes: (93)-SGLDG, (174)-KGEAG and (843)-EGSPG, where the numbers in parentheses are the residue numbers of the first residue in a pentamer (mutable glycine residues are underlined).

The replacement of Gly by Cys is found to cause delayed helix formation by 5 to 60 minutes (Raghunath et al., J. Mol. Biol. 236: 940–949, 1994). As expected, the disease severity increases if mutations occur near the nucleating C-terminus. However, in the limited number of mutant collagen experiments conducted, the contexts around these mutant glycine residues show that the "mild" cases are associated with prime GXZ, as shown in the following table.

TABLE 9

Gly → Cys Mutations in Human a1(I) Chain

| Residue No. | Context | OI severity | Delayed helix time (min.) |
|---|---|---|---|
| 94 | fSGLd | mild | 5 |
| 223 | nGAp | mild | 20 |
| 526 | ApGNd | mild | 5 |
| 691 | AgpP | severe | 30 |
| 988 | ppgpr | severe | 60 |

Both the delayed helix formation time and prime property correlate well with disease severity; but the distance to the C-terminus fails the correlation with one exception at Gly (526).

As stated earlier, the collagen triple helix is formed by a zipper mechanism nucleating from the C-terminus (Byers, 1990). If any one of the three glycine residues in three terminating PPGPP overlaps is mutated, the triple helix may not be able to form. Mutation to Cys, or other bulky residues, may simply create a "kink" in the triple helix. Given time, the kinks can be overcome by zipping with hydrogen bonds formed between interchain glycine residues (Raghunath et al., 1994).

VII. Coiled Coil Heptads

As stated above, a huge number ($20^7$) of possible "words" can be formed with seven amino acids. With this number of iterations, calculation shows that 344,898,296 are prime heptapeptides. This gives a probability of finding a prime heptapeptide at random as 0.27. This fraction is smaller than 0.38 for random prime tripeptides and 0.30 for random prime pentapeptides. On the other hand, the argument given in the last two sections suggests that heptapeptides with hydrophobic amino acid residues at positions 1 and 4 have a high chance of being prime. Long, uninterrupted coiled coils are models to test this argument.

The entire sequence of the 7-segment, 6-period heptads in tropomyosin (McLachlan et al., J. Mol. Biol. 98: 281–291, 1975)—a coiled coil—is shown in FIG. 4, with the prime oligomers highlighted in capital letters by starting the z-sum from the first residue in a heptad. There are 41 heptads, 31 having hydrophobic residues at the 1,4 positions, and 22 prime "heptads" (with length ranging from five to eight residues). The prime fraction 22/41 is larger than 0.5 in this chain. The data also show a majority of prime heptapeptides in segment II, which turns out to be the "most typical segment" or the closest to an ancestral segment found by a much more complicated computation (McLachlan et al., 1975). If the numbers of higher prime oligomers is used as a measure of the degree of similarity to the ancestral segment, the order deduced from FIG. 4 is

II>I>VI>III>IV>V>VII

This order shows that most primes are present in the first half of the molecule. This result differs slightly from that of McLachlan et al. (1975) who concluded with the order as II>VI>III.

VIII. An Ancient Protein

The ancient ferredoxin protein might have the repeats of AD(P)SG, where the second residue can be D or P, as discovered by Eck and Dayhoff (1966) who pointed out this sequence might have existed before complex amino acids and before the genetic code took its current form. Writing this tetramer repeat with alternating D and P as the second residue, the trimer, pentamer, heptamer, . . . all take prime z-sums:

z (ADS)=113; z (ADSGA)=227; z (ADSGAPS)=269 z (ADSGAPSGA)=383, z (ADSGAPSGADS)=443, . . .

Not until 17-mer does the series reach a nonprime z-sum (713). It then returns to prime numbers for 19-mer, 21-mer, etc. The Ala residue is a proper starter for tetramer repeats and this series seems to suggest that high prime propensity might be an ancient strategy for propagation. The abundant prime tripeptide GAP in collagen sequences is also present in this ancient sequence. The modern form of ferredoxin has lost its prime propensity somewhat. Mutation and evolution not only randomize regularity of repeats, but also reduce prime propensity.

IX. Nonprime Tripeptides

The majority of calculated examples in previous sections are carried out for a single protein with long, patterned and uninterrupted chains. Even though this method is first applied to collagen repeats, extension to pentapeptides, heptapeptides and non-collagen sequences immediately follows. Furthermore, the simplicity of this method affords a rapid test on statistically derived sequence motifs, with or without a broader context. For example, in a database with redundancies carefully screened out, Doolittle ("Redundancies in Protein Sequences," Chap. 14, pp. 599–623, in Fasman, G.D. Ed., "Prediction of Protein Structure and the Principles of Protein Conformation,", Plenum Press, New York, 1989) listed five "underrepresented" tripeptides that turn out to be nonprime:

| Tripeptide | z-sum |
|---|---|
| ikl | 26 |
| rfe | 121 |
| rat | 95 |
| esk | 95 |
| res | 125 |

These tripeptides are underrepresented in both directions, i.e., ikl and lki are both rare. However, the "underrepresented tripeptides one-way only" (not shown here) contain primes. In the same work, the 18 most favorable tripeptides in β turns are also listed, but only two of them are found to be prime tripeptides; twelve tripeptides are the "obvious" nonprimes (numbers ending in 5, as 95 and 125 in the above table). Chou and Fasman (1978) listed Gly, Pro, Asn, Asp as the most likely candidate residues in turns or bends. The low prime propensity of GXP has been noted before, but z(GNP)=85 and z(GDP)=105 are also obviously nonprimes. From the last examples it appears that nonprime triplets may be associated with rare occurrence or with the geometry of β turns.

X. Prime Peptides and Conformation

This connection with geometry in turn leads to a re-examination of the famous "same sequence-different conformation" example given by Kabsch and Sander (Proc. Natl. Acad. Sci., USA 81: 1075–1078, 1984). In their second- and third-to-last entries, under the heading of "similar conformation," the pairs of identical pentamers are in the helical conformation:

TABLE 10

Sequences and Conformation

| Pentamer Pairs | Protein | Prime z-sum |
|---|---|---|
| AAKFE sn (hhhhh ts) | Lysozyme (hen) | 5-mer = 197 |
| AAKFE rq (hhhhh hh) | Ribonuclease-s | |
| AALVK SS (hhhhh hh) | Leghemoglobin | 7-mer = 229 |

TABLE 10-continued

Sequences and Conformation

| Pentamer Pairs | Protein | Prime z-sum |
| --- | --- | --- |
| AALVK MR (hhhhh hh) | Cytochrome | 7-mer = 211 |

Table 10 lists the "same" pentamers plus two more residues. The parentheses enclose conformation notations for each residue: h=helix, t=turns and s=bend or space. Both pairs of pentamers have hydrophobic residues at the 1,4 positions and the extended heptapeptides satisfy the requirements of coiled coil heptads. However, the first pair only gives an identical prime pentamer, while the second pair has two prime heptapeptides with the "same" helical conformation in every residue.

The self/nonself discrimination in immunology can be treated the same way. In three host proteins and one viral protein studied by Ohno (Proc. Natl. Acad. Sci. USA 88:3065–3068, 1991) the long, Met-containing oligopeptides were found to be pentamer z (ASGMA)=199 and heptamer z (PSPLMLL)=109. Both peptides are prime and "self" —shared by host proteins. Furthermore, isoleucine appears four times in the 18-residue-long, nonself region of the virus, but none of its Ile-containing tripeptides were found in the three host proteins. The number equivalence of this "nonselfness" imparted by isoleucine is that tripeptides containing one Ile residue cannot form a prime z-sum. Likewise, the "hypervariable" β arches in a "dimpled β helix" comprise an octapeptide RHINITIS (Cohen, Science 260:1444–1446, 1993) with a high Ile content such that none of the tripeptides can form a prime.

XI. Runs of Identical Amino Acids

In one of Doolittle's tables (1989), longest runs were identified for all 20 amino acids. The lengths of long runs appear to be limited by the natural abundance of each amino acid. However, the longest runs of Gln and Glu are even longer than those of more abundant amino acids. Runaway runs of Gln have been implicated in the development of the Huntington's disease (MacDonald et al., Cell 72:971–983, 1993). Runs of the less abundant amino acids are explicable with either the formation of a prime peptide or a high prime propensity.

The longest Trp run is WWW, and z(WWW)=3 is itself a prime number. The length of 3 is attainable by this least abundant amino acid. No runs of other amino acids can reach a prime number.

The longest Met and Ile runs (Doolittle, 1989) are MMMM and IIIII; both have the maximum prime propensity, pp(12)=0.65. The Ile hexamer readily forms a prime with one more residue (Broglie et al., Proc. Natl. Acad. Sci., USA 83: 6820–6824, 1986): z(IIIIIN)=23. But MMMM does not reach a prime pentamer or heptamer downstream (George et al., EMBO J. 4: 1199–1203, 1985): It is only four residues away from the N-terminal Met and the context surrounding this tetramer is given by

MKKNRMM MMIWSV . . .

The tetramer run is split into two MM dipeptides: One belongs to a prime heptamer and the other heads a prime hexamer. Both MMMM and IIIII are even-number runs with the same z-sum and same prime propensity, again suggesting a similar property and function of Met and Ile, especially in the initiation of peptide synthesis or as "starters" of heptad repeats and prime heptapeptides. This similarity also leads to a new method for the alignment of transmembrane helical sequences (see Section XIII below).

The longest run of Lys is also a hexamer and pp(KKKKKK)=pp (42) is again 0.65. This hexamer readily takes up a Ser residue (Watson & Dixon, Biosci. Reports, 1: 167–175, 1981) to become a prime heptamer: KKKKKKS (z=71).

XII. Protein Huntingtin

The protein product ("huntingtin") of the Huntington's disease gene has long runs of Gln and Pro (MacDonald et al., 1993). Individuals not affected by the disease have a typical segment of $Q_{23}P_{11}$. Forming a run is a sure way to avoid reaching a prime number but it may cause instability to the entire protein chain. In this "normal" run, the DP values of Gln and Pro, 23 and 11, invite comparison with those in $E_{25}D_{11}$, an acidic segment in the high-mobility-group protein from calf (Wharton et al., Cell 43: 567–676, 1985): The similarity between Gln and Glu is obvious and well-known; and Asp has been implicated as a substitute for Pro in ancient ferredoxin (Eck & Dayhoff, 1966). The z-sums of these two segments are $$z(Q_{23}P_{11})=580$$

$$z(E_{25}D_{11})=1816$$

Both numbers are not divisible by 6 and therefore these two segments are not high pp oligomers. However, both segments reach prime number z-sums with only one more amino acid (MacDonald et al., 1993; Watson & Dixon, 1981):

$$z(Q_{23}P_{11}Q)=599$$

$$z(E_{25}D_{11}K)=1823$$

The maximum DP for Glu and Gln runs were quoted as 25 and 31 by Doolittle (1989). Both numbers are incorrect since the original work lists an even longer Glu run (George et al., 1985) of $E_{27}$ and the Gln "run" is actually $Q_{13}HQ_{17}$ which is itself (Wharton et al., 1985) a prime 31-mer. But this value of the Gln run length turns out to be the "threshold" DP at and below which a functional protein can tolerate, as 31 is the next number beyond 23 to form a prime number with $P_{11}Q$, that is $$z(Q_{31}P_{11}Q)=751$$

In general, in $Q_mP_{11}Q$, when m=1, 5, 13, 19, 23, 31, 35, 41, 49, 59, 61, 71, 73, 79, 85, 101, 113, 115, 119, 133, . . . the z-sums reach a prime number. A repeat of 37 Gln residues appears to separate the "normal" range from the "Huntington's disease" range (Martin, Science 262: 674–676, 1993). A long Gln run is also found in the androgen receptor, with a threshold DP listed as 30 for the Kennedy's disease (Martin, 1993; Biancalana et al., Huaman Mol. Genet. 1: 255–258, 1992).

The discrepancy between the thresholds in these two diseases is small but probably significant: Near the N-terminus of the putative "huntingtin" are two Met residues, each heading a heptamer. The initial part of this protein (MacDonald et al., 1993) is given by

| | | | | | | |
|---|---|---|---|---|---|---|
| MATlekl | MKAFESL | KSFQQQQ | $(Q_{n-4}P_{11}Q)$ | | | |
| | | | LPQPPPQ | APLLPqp | QPPPPPP | PPPPGPA... |

The maximum number of prime heptapeptides is generated by writing the protein this way. Here four Gln residues have been counted as part of the prime heptamer preceding the peptide in the parentheses. Assuming the maximum run length is the longest run tolerable in a functional protein, then n−4=31 or n=35 which is approximately the upper bound found for the normal Gln runs in several diagnostic studies (Read et al., Nature Genet. 4: 329–330, 1993; Dayao et al., Nature Genet. 4: 387–392, 1993; Snell et al., Nature Genet., 4: 393–397, 1993; Andrew et al., Nature Genet. 4: 398–403, 1993).

In the case of the androgen receptor protein, the Gln run is located near the C-terminus (Martin, 1993). Thus the maximum run length of 31, unsplit, is directly applicable to this protein. Expansion beyond 31 Gln residues may develop the Kennedy's disease (Biancalana et al., 1992).

The Gln runs are encoded by the trinucleotide CAG repeats. Other disease-causing nucleotide repeats include those of CTG and CGG, in noncoding regions of the genes (Martin, 1993). Ohno has shown that complementary trinucleotides CTG and CAG are utilized extensively in the DNA language, in both protein-coding and noncoding regions (Ohno, 1988).

The structure of poly-Gln proposed by Perutz et al. (Proc. Natl Acad. Sci.USA 91:5355–5358, 1994) is that of a "polar zipper" formed by linking β strands together into sheets or barrels through networks of hydrogen bonds.

XIII. Glucose Transport Proteins

A sugar transport protein has "6+6" hydrophobic segments spanning the cell membrane, with a long stretch of hydrophilic region separating the left six from the right six helices. Since each segment contains three heptapeptides, it is reasonable to assume that each heptapeptide is headed by Leu, Ile or Met, as in coiled coils and leucine-zippers.

Five homologs of glucose transport proteins were analyzed by Henderson (Res. Microbiol. 141: 316–328, 1990) and their hydrophobic segments, Nos. 1–12, were given in his paper. Almost all of these are 21-residue, 3-heptamer segments, except seven of them are hexamers. Thus the total number of residues is 5×21×12−7=1253. It can be readily verified that the number of prime hexamers and prime heptamers is 54. The conventional method of aligning the homologous sequences maximizes the number of "absolutely conserved" residues. This number is 33. There are 182 Leu residues, making a frequency of $182/1253=0.145$. There are 172 Ile and Met residues, with a frequency of $172/1253=0.137$. On comparison with the fraction $1/7=0.143$, one may assume that there is one Leu or one (Ile+Met) in every heptad. However, the distribution of Leu is extremely uneven, ranging from 4 in five segments of No. 4, to a maximum of 32 in No. 6 segments. The (Ile+Met) starters are much more evenly distributed. There are 16 columns with at least one (Ile+Met) starter. These data suggest that an (Ile+Met) head is the most probable starter in "heptads" of such helical segments.

With this result, another alignment table is constructed with (I+M) as starters and the maximum number of prime oligomers, as shown in FIG. 5 here. The total number of residues in this figure is 1233. Total number of (I+M)=179 and its fraction is $179/1233=0.145$, or approximately 1/7. Total number of absolutely conserved residues, marked by * in FIG. 5, is 29. Total number of prime hexamers and up=55. But the number of (I+M) columns is 31—out of the total 36 columns.

The "heptads" with I+M heads actually have a peptide size ranging from 5 to 8. As a consequence of using the I+M starters and prime oligomers, there is a slight reduction (29 from 33) in the number of alignment of absolutely conserved residues, but a large increase of (I+M) starter columns (31 from 16). The majority of the segments listed have 6k oligomers. Alignment of (I+M) starters implies that, in each 21-residue segment, (I+M) heads periodically generate three "heptads" on average. This is a new method for alignment of transmembrane segments. The implication of an (I+M) head also means that these two residues are hydrophobic helix starters, much like their function as initiators in the translation of protein from nucleotides. Even though Ile and Met are incompatible with other residues in forming "6k dimers" (see above), they have a better chance of heading a prime "heptad" because their small z values give smaller z-sums with a higher density of primes. When three or more consecutive heptad starters are replaced by Leu residues, the result is a leucine zipper.

XIV. β AMYLOID PROTEIN

Amyloid formation is the result of lateral interaction between protein chains. This phenomenon belongs to the general case of polymer crosslinking and gelation (Yan, J. Chem. Phys. 78: 6893–6896, 1983). Insoluble, rigid amyloids may deposit onto the cell surface and become detrimental to the cell. When nerve cells are coated with amyloids, the result is Alzheimer's disease. In the amyloid precursor protein, the so-called β-amyloid starts at Asp(672) and runs through Thr(714) of the protein, as the portion enclosed by the square brackets below:

| | | | | |
|---|---|---|---|---|
| (669)-vkm | [DAEFRHD | SGYEVhh | QKLVFpa | EDVGSNK |
| | | | (AD)-g | Q-(CA) |
| | | | | g-(?) |
| | //GAIIGLM | VGGvvi | ATVIVIT] | LVMl//kkk-(726) |
| | | (SZ)-V | f-(AD) | |
| | | | g-(AD) | |
| | | | i-(AD) | | where the abbreviations for the disease names are: AD=Alzheimer's disease; CA=cerebral congophilic angiopathy; SZ=Schizophrenis; ?=unknown cause. Amino acids written below the mutated ones are capitalized if the resultant hexamers or heptamers are primes, otherwise they are in lowercase letters. Two // symbols confine the transmembrane domain (Hardy, Nature Genet. 1: 233–234, 1992). The heptads inside this domain are all patterned with hydrophobic residues at positions 1 and 4, perfectly matching this "reading frame" and boundaries of prime heptads. The prime fraction in β amyloid protein is 0.5.

In "reading" this sequence, the definition of the molecule as the region starting from Asp(672) should be adhered to. If Met(671) is counted as a heptad starter, the sequence would have fewer primes:

| | | | | |
|---|---|---|---|---|
| mdaefrh | DSGYEVH | HQKLVfp | aedvgsn | |
| | | k//gaiig | mvggvi | ATVIVIT LVMl//kkk |

Furthermore, with this reading frame the transmembrane domain no longer starts with a prime heptad.

Another gelling molecule is fibrinogen, which forms blood clots. The entire sequence has 88 "heptads," 29 of them primes if counted from the first residue listed (Doolittle et al., Nature 280: 464–468, 1979). However, there are ten 13-mer repeats ending mostly with Trp (underlined), and five of the 13-mers are primes:

| | | | |
|---|---|---|---|
| TESPINPssagsw | NSGSSGPGSTGnr | NPGSSGTGSGATW | KPGSSgpgstgsw |
| NSGssgtgstgnq | NPGSPrpgstgtw | NPGSSERGSAGHW | TSESSVSGSTGQW |
| HSESGSFRPDSPG | SGNARPNDPNWGT | | |

This high prime 13-mer fraction region also has a high density of glycine and GA/GS dipeptides. All are known to nucleate hydrogen bond zippers. (Counting Trp as the head or central residue would not generate a high prime 13-mer fraction.)

Amyloid formation, blood clotting or gelation are inevitably formed by lateral hydrogen bonding. The individual protein chains are usually in the extended form of β strands, with zipping made through hydrogen bonds. The same can be said about silk fibroin protein and the three chains in the collagen triple helix, where zippers may not lie on the same plane as does a β "sheet." All these are hydrogen bond zippers, as opposed to the hydrophobic bond zippers of leucine zippers and coiled coils.

XV. Hydrogen Bond Zippers and Prions

From the last section, it is obvious that protein chains forming hydrogen bond zippers have a wide variety of repeating patterns and various hydrogen bond densities along the zippers. Strongly patterned are poly-Gln in protein huntingtin (which may have "polar zipper" structure (Perutz et al., 1994) formed by hydrogen bonds between main-chain and side-chain amides), silk fibroins and collagen triplets, with runs or repeats of an amino acid, dipeptides and tripeptides, respectively. Fibrinogen has a patterned region of high prime 13-mer fraction. These chains also have a high Gly content to crosslink laterally with each other through hydrogen bonds.

On the other hand, without the obvious repeats such as poly-Gln, collagen, etc., β amyloid protein also gels through hydrogen bonding. Before gelation (or amyloid formation) occurs, the individual chains must first assume extended β strand conformation. The embeded transmembrane domain then sets itself free from the helix conformation and begins nucleating the hydrogen bond zipper with its glycine contacts. This mechanism may be called "combing," meaning stretching out the helices and kinks along the chains to become β strands, which then interact laterally to form amyloid.

Both α helix and β sheet are the "regular structures" in proteins. Most of the above demonstrations are examples of regular structural elements for fibrous proteins, i.e., chains without turns or bends. Primordial DNA probably grew by simple base repeats, in protein-coding region this would result in regular (αhelix and β strand) structures, as demonstrated by ohno and Epplen (Proc. Natl. Acad. Sci., USA 80: 3391–3395, 1983). In a modern fibrous protein, the first half of the molecule always has more regular and more prime "heptads," than the second half, as evidenced from all the above examples. Regularities in structure (Ohno & Epplen, 1983) and in prime heptads, and the z-numbers themselves (Yan et al., 1991), can all be traced back to the coding "history" written by DNA sequences.

Writing as eight heptads, the ancient ferredoxin appears as
ADSGAPS gadsgap SGADSGA PSGADSG
APSGADS gapsgad sgapsga DSGAPSG That is, five out of eight heptads are primes. The complete sequence of modern ferredoxin (Eck & Dayhoff, 1966), on writing as consecutive heptads, also has five primes out of eight heptads:

AYKIADSC VSCGAca SECPVNA ISQGDSI
FVIDADTC IDCGnca NVCPVga PVQe

The duplication of the two halves of the molecule is obvious in the two lines above. Protein growth always start with regular structural entities, with high prime heptad fraction, and then decrease in regularity and in prime propensity as a result of duplication, mutation, deletion or addition, etc. The development of protein language is therefore analogous to that in human: from simple "Ma Ma" and "Pa Pa" (dipeptide repeats) to repeating trimers, to tetramers, to the sophisticated "seven-word" poems as those by Li Bai (patterned and prime heptads). Consecutive prime heptads are implicit repeats. This implication is made obvious with prion proteins, as follows.

Prion proteins are interesting virus particles because they do not have DNA or RNA. Their replication and amyloid formation cause diseases in animals and humans (Huang et al., Proc. Natl. Acad. Sci. USA 91:7139–7143, 1994; Pan et al., PNAS-USA 90:10962–10966, 1993; Kocisko et al., Nature 370:471–474, 1994). All known amyloids are protein aggregates with an extensive β sheet secondary structure. But there are predictions that cellular (soluble) prion proteins may have several regions of α-helices (Huang et al., 1994). The transition from α helix to β sheet structures has been postulated as a possible cause of "prion diseases" (Pan et al., 1993).

Using the method of "prime heptad scan" outlined above, the consecutive heptads are depicted in FIG. 6 for hamster and human prion protein chains. Each heptad is designated with its z-sum, which is marked with a prime sign (') if it is a prime number. The structure is a highly regular one for the following reasons: (i) Each chain has 19 primes, out of a total of exactly 36 "heptads."The prime fraction is greater than 0.5, and these molecules are most likely long chains without interruption, bending or turning. (ii) The first halves of these prion sequences have a slightly larger prime fraction than the second halves. (iii) The prion gene is contained in a single exon (Huang et al., 1994). All these characteristics also show that prion proteins are of an ancient origin.

Therefore, prion proteins are fibrous chains like those in Type I collagen, silk fibroin, fibrinogen, or tropomyosin. With the exception of tropomyosin, all these fibrous protein strands aggregate through hydrogen bond zippers. (Interactions between helical strands of tropomyosin are caused by hydrophobic or dispersion forces, which differ from the hydrogen bonds in "hydrogen bond zippers." The "hydrophobic bond zippers" may bind two, three or four strands as a "bundle" as in tropomyosin coiled coil, isoleucine and leucine zippers (Harbury et al., Science 262: 1401–1407, 1993), but such bundles cannot form amyloid or gel.) The gelling proteins—fibrinogen, β amyloid, and prions—are either wound-healing or disease-causing agents.

In FIG. 6, the identical, continuous prime heptad segments are also highlighted with the (+,−,0) dipeptide compatability notation, where (+)=6k+1 Type, (−)=6k−1 Type and 0=Ile, Met and Cys. In the human prion chain, six heptads are found to be in the "1,4-hydrophobic" pattern: MANLGCW, MLVLFVA, AGAaaag, MERVVeq, VILLIsf and LIFLivg. The first two are the "initiation" prime heptads, again suggesting a higher tendency of the first half of the protein to propagate with a regular structure. The third heptad, AGAaaag, may be a nucleation site for amyloid formation (Pan et al., 1993). The first continuous stretch of primes, with four repeats of the octomer WGQPHGGG, behave like the octomer repeats in the ancient ferredoxin in generating high fractions of prime heptads, also has a high glycine density to nucleate hydrogen bond zippers. The zipper mechanism starts at these nucleation sites. Helical segments, whether predicted to exist as patterned heptads, or as helices with various lengths as predicted with techniques used for globular proteins (Huang et al., 1994), would have been "combed" straight before or during amyloid formation.

Since the same sequence (primary structure) cannot predict two forms of secondary structure, to account for the eventual amyloid formation, Pan et al. (1993) also proposed an α helix to β sheet conversion mechanism. The term "combing" used in this paper implies an external action on this conversion. Indeed, in a demonstration of cell-free formation of prion amyloid, a large amount of pre-existing prion aggregates is required as catalysts or seeds (Kocisko et al., 1994) which may be the source of this external force.

XVI. Conclusions and Summary

Proteins are always described with a multi-level structure. Paradoxically, the molecular geometry approach, which deals with the fine details of side-chain size and shape, is effective only at the level of tertiary structure (Harbury et al., 1993). The primary structure or sequence specificity, connectivity and compatibility in proteins have eluded the treatment of molecular geometry for a long time. But a sequence analysis method must first deal with these "intrinsic" properties of a protein chain.

Although the number code described above is invented to interpret the primary structure (sequence language) of proteins, patterns for specific groups of side-chains and the secondary structure emerge naturally: dipeptide compatibilty, prime GXP for small side-chains, PGXPG for aromatics, XPGXPGX for hydrophobic amino acids in positions 1,4,7 of a heptad, high prime heptad fractions, etc. Statistical methods, the other non-geometrical technique, are always hindered by the size and redundancy of databases (Doolittle, 1989). The $20^3$ possible tripeptides and $20^5$ pentapeptides may have enough sequence data for statistical analysis on a given species. But $20^7$ heptapeptides are beyond the scope of databases to be provided for by the Human Genome Project. The number code to protein sequences has accounted for the "intrinsic" specificity and stability in prime tripeptides and heptapeptides, and in the high-pp dipeptides and hexapeptides complementary to these primes. In contrast, runs of identical amino acids, unable to form primes, could readily render their parent protein unstable or nonfunctional, once expanding beyond a certain threshold DP. All these sequence characteristics can be inferred from the corresponding number properties.

Two theorems have been used as the grammatical rule for the protein language. Both are originated from the unique set of amino acid numbers listed in Table 2. The amino acid numbers are specific, unique and universal, e.g., z (Gly)=61, which does not change with its conformational states. The utility of this number code is demonstrated with extensive examples: compatibility in dipeptides, reading frames in triplet repeats, mutations in collagen, coiled coil patterns, tetrapeptide or octopeptide repeats in ancient ferredoxin, nonprime tripeptides in turns or bends, primes as constraints to runs of amino acids, etc. The demonstrated or proven techniques are then used to "fine tune" mutational and conformational data interpretation. Helical heptad patterns are exemplified by the hydrophobic 1,4 positions (coiled coil), L7 heptads (isoleucine and leucine zippers) and (I+M)-headed hydrophobic heptads (glucose transport protein). High prime heptad fractions are indicative of a regular structure, appearing mostly in the first half of a fibrous protein. Hydrogen bond zippers are nucleated from the high glycine content, consecutively prime regions. Patterned helical segments in amyloid and prion proteins can be overcome or "combed" straight by the hydrogen bond zipper mechanism. All these examples illustrate that numeric patterns manifest structural patterns.

I claim:

1. A process for evaluating a nucleotide sequence, comprising:
   (a) determining by conventional means the nucleotide sequence of an oligomer consisting essentially of nucleotides;
   (b) assigning each nucleotide an n-number, wherein Adenine (A) equals zero (0), Cytosine (C) equals one (1), both Thymine (T) and Uracil (U) equal two (2), and Guanine (G) equals three (3) to derive an n-number sequence representative of the nucleotide sequence;
   (c) entering said n-number sequence into a database to derive an n-number library;
   (d) specifying a property of a nucleotide sequence derivable from n-numbers;
   (e) scanning the n-number library for all possible n-number sequences which satisfy the specification; and
   (f) displaying the resultant n-number sequences.

2. The process in claim 1 wherein the resultant n-number sequences are represented in a manner selected from a group consisting of plotting n-numbers versus n-number populations, and plotting n-numbers versus frequency of n-number occurrence.

3. The process in claim 1 wherein one of the following evaluations is performed:
   (a) adding the values of n-number dimers, with n-number dimers attaining values of 1,3 and 5 predicted to be more frequent and more stable, n-number dimers attaining values of 1, 3 and 5 headed by a purine (A=0, G=3) predicted to be non-coding splice termini, and n-number dimers attaining values of 2 and 4 predicted to be less frequent, less stable, subject to mutation and possibly representing stop codons;
   (b) scanning the n-number library for contiguous n-number sequences adding up to primes, with prime n-number sequences predicted to be more highly conserved and possibly having special function; and
   (c) scanning the n-number library for polyrepeat patterns which may be indicative of enhanced mutability, special function, higher degree of conservation and evolutionary strategy, with poly-GC (poly 3-1) dimers predicted to have evolved into the synonymous quartets of amino acid codons (those triplets in which the identity of the third codon is insignificant) by acquiring weak-bonding single base substitutions and poly AU (poly 0-2) dimers predicted to have evolved into unique or doublet amino acid codons by acquiring strong-bonding substitutions.

4. A process for evaluating an amino acid sequence, comprising:
   (a) determining by conventional means the amino acid sequence of a polypeptide or its precursor DNA or RNA sequences;
   (b) assigning each amino acid or codon a z-number, wherein a stop codon equals zero (0), tryptophan (Trp)

equals the non-prime odd number one (1), isoleucine (Ile) equals the prime number two (2), methionine (Met) equals the prime number three (3), threonine (Thr) equals the prime number five (5), lysine (Lys) equals the prime number seven (7), asparagine (Asn) equals the prime number eleven (11), proline (Pro) equals the prime number thirteen (13), leucine (Leu) equals the prime number seventeen (17), glutamine (Gln) equals the prime number nineteen (19), serine (Ser) equals the prime number twenty-nine (29), aspartate (Asp) equals the prime number thirty-one (31), arginine (Arg) equals the prime number thirty-seven (37), valine (Val) equals the prime number forty-one (41), tyrosine (Tyr) equals the prime number forty-three (43), histidine (His) equals the prime number forty-seven (47), alanine (Ala) equals the prime number fifty-three (53), glutamate (Glu) equals the prime number fifty-nine (59), glycine (Gly) equals the prime number sixty-one (61), phenylalanine equals the non-prime odd number twenty-five (25), and cysteine equals the non-prime odd number forty-five (45) to derive a z-number sequence representative of the amino acid sequence;

(c) entering said z-number sequence into a database to derive a z-number library;

(d) specifying a property of a polypeptide sequence derivable from z-numbers;

(e) scanning the z-number library for all possible z-number sequences which satisfy the specification; and (f) displaying the resultant z-number sequences.

5. The process in claim 4 wherein the resultant z-number sequences are represented in a manner selected from a group consisting of plotting z-numbers versus z-number populations, plotting z-numbers versus frequency of z-number occurrence, and translating z-numbers into correlating structural motifs, structures, turns and bends.

6. The process in claim 4 wherein one of the following evaluations is performed:

(a) scanning the z-number library for contiguous z-number sequences summing to primes, with prime z-number sequences predicted to be more highly conserved and more likely to exhibit special function;

(b) identifying prime z-number heptamers with an initiation Met (3) residue, predicted to initiate leucine zippers and coiled coil segments, and predicted to be membrane spanning helices when configured as 3-heptad, 21 residue segments;

(c) identifying prime z-number hexamers or octamers with an initiation Ile (2) residue, predicted to be membrane spanning helices when configured as approximately 3-heptad, 21 residue segments;

(d) identifying prime z-number heptamers with an initiation Leu (17), predicted to initiate coiled coil segments and leucine zippers;

(e) identifying prime z-number heptamers with hydrophobic moieties at positions 1 and 4, predicted when repetitive to be coiled coils and leucine zippers;

(f) identifying prime z-number sequences having lengths of 5, 7 and 13 moieties by the presence of a central moiety selected from a group consisting of Trp (1), Phe (25) and Cys (45), predicted to be highly conserved and, when headed by a starter moiety selected from a group consisting of Ile (2) and Met (3), predicted to be active in protein folding;

(g) identifying possible cysteine switches by the presence of Cys (45) as a central moiety in a prime z-number sequence;

(h) identifying possible zinc fingers by the presence of two adjacent prime z-number sequences, each having a central His (47) moiety;

(i) identifying potential mutational hotspots by the presence of a prime z-number sequence having a central moiety selected from a group consisting of Cys (45) and Arg (37);

(j) identifying possible beta turns by the presence of non-prime trimers;

(k) scanning the z-number library for repetitive sequences, indicative of high degrees of conservation and functional importance;

(l) scanning the z-number library for overlapping prime pentamers in which each subgroup of three adjacent moieties sums to a prime, predicted to have possible utility in drug transport;

(m) scanning the z-number library for heterodimeric prime z-number pairs differing by 2, predicted to be abundant particularly when their sum is divisible by 6;

(n) scanning the z-number library for homodimeric prime z-number pairs, predicted to be abundant particularly when their sum is divisible by 6;

(o) in a z-number library containing collagen sequences, scanning for prime GXZ sequences with mutated Gly residues, predicted to correlate with delayed helical formation;

(p) in a z-number library containing collagen sequences, scanning for prime tripeptides, predicted to be more abundant than expected by random association;

(q) in a z-number library containing Type I collagen sequences, identifying prime tripeptides GAR, GAP and KGE, predicted to be more abundant than their nonprime analogs gak, glp and kgd;

(r) in a z-number library containing Type IV collagen sequences, identifying prime tripeptides DCG, predicted to be more abundant than their nonprime analogs ecg;

(s) in a z-number library containing fibrinogen sequences, predicting the reading frame by identifying prime 13-mers ending with Trp residues;

(t) identifying high fractions of prime heptapeptides in implicit repeat patterns, predicted to signify regular structural (α-helix and β-sheet) motifs;

(u) identifying high Gly-fraction, high prime heptapeptide fraction sequences, predicted to signify gelling molecules with β-sheet conformation (prion proteins);

(v) in a library containing β amyloid protein sequences, predicting protein boundaries based on the reading frame generating the greatest number of prime heptapeptides;

(w) identifying homoheptapeptide runs of hexa-Ile and hexa-Lys, predicted to have high prime propensity (ability to achieve a prime number with the addition of another moiety);

(x) identifying hexapeptides with sums divisible by six as high prime propensity sequences with enhanced ability to achieve a prime number with the addition of another moiety;

(y) assessing polyrepeat sequences for maximum stable length by determining polyrepeat lengths divisible by six and having high prime propensity (ability to achieve a prime number with the addition of another moiety);

(z) assessing the stability-enhancing properties of interruptions in polyrepeat sequences by determining their influence on divisibility by six and prime propensity in the polyrepeat sequence; and (aa) identifying prime tripeptides and prime hexapeptides whose prime sums fall within a decade of prime quartets (clusters of four primes within a span of ten consecutive numbers), predicted to have enhanced stability and enhanced abundance.

7. A process for evaluating the secondary structure of an RNA moiety, comprising:

(a) determining by conventional means the RNA cross-linkages resulting in a secondary RNA structure;

(b) assigning to each cross-linked RNA pair within the structure a p-number, wherein G:C is three (3), A:T is two (2), G:T is one (1), and base pairs other than G:C, A:T, and G:T have a value of zero (0) to derive a p-number sequence representative of the RNA cross-linkage sequence;

(c) entering said p-number sequence into a database to derive a p-number library;

(d) specifying at least one property of RNA secondary structure derivable from p-numbers;

(e) scanning the p-number library for all possible p-number sequences which satisfy the specification; and (f) displaying the resultant p-number sequences.

8. A process for generating novel oligopeptide sequences, comprising:

(a) specifying a property of an oligopeptide sequence derivable from z-numbers;

(b) combining z-numbers in all possible configurations which satisfy the specification; and (c) displaying the resultant z-number sequences.

9. The process in claim 8 wherein the resultant z-number sequence is translated into a representational model selected from a group consisting of a regular structural sequence, computer model and mechanical model.

10. A process for evaluating an amino acid sequence, comprising:

(a) determining by conventional means the amino acid sequence of a polypeptide or its precursor DNA or RNA sequences;

(b) assigning each amino acid or codon a 6k-type, wherein 6k+1 is assigned to the amino acids tryptophan (Trp), lysine (Lys), proline (Pro), glutamine (Gln), phenylalanine (Phe), aspartate (Asp), arginine (Arg), tyrosine (Tyr) and glycine (Gly), 6k-1 is assigned to the amino acids threonine (Thr), asparagine (Asn), leucine (Leu), serine (Ser), valine (Val), histidine (His), alanine (Ala) and glutamate (Glu), 6k+2 is assigned to the amino acid isoleucine (Ile), and 6k+3 is assigned to the amino acids methionine (Met) and cysteine (Cys), to derive a 6k-type sequence representative of the amino acid sequence;

c) entering said 6k-type sequence into a database to derive a 6k-type library;

(d) specifying a property of a polypeptide sequence derivable from the 6k-type sequence;

(e) scanning the 6k-type library for all possible 6k-type sequences which satisfy the specification; and (f) displaying the resultant 6k-type sequences.

11. The process in claim 10 wherein one of the following evaluations is performed:

(a) scanning the 6k-type library for 6k+1/6k-1 heterodimers, predicted to have increased pairing compatibility, increased stability, increased frequency in ancient proteins and in abundance signifying a possible protein with enhanced tensile properties;

(b) scanning the 6k-type library for 6k+2 and 6k+3 moieties, predicted to have reduced pairing compatibility with other moieties, signifying possible initiation sites for protein synthesis, and signifying possible start sequences for hydrophobic helical heptads; and (c) in 6K-type libraries containing silk fibroin sequences, identifying 6k+1/6k-1 heterodimers GA and GS, predicted to be abundant and to contribute to tensile strength.

12. A method of determining secondary and/or tertiary structure of a protein or peptide comprising determining the amino acid sequence of said protein or peptide, assigning a z-number to each amino acid wherein tryptophan (Trp) is assigned non-prime odd number one (1), isoleucine (Ile) is assigned prime number two (2), methionine (Met) is assigned prime number three (3), threonine (Thr) is assigned prime number five (5), lysine (Lys) is assigned prime number seven (7), asparagine (Asn) is assigned prime number eleven (11), proline (Pro) is assigned prime number thirteen (13), leucine (Leu) is assigned prime number seventeen (17), glutamine (Gln) is assigned prime number nineteen (19), serine (Ser) is assigned prime number twenty-nine (29), aspartate (Asp) is assigned prime number thirty-one (31), arginine (Arg) is assigned prime number thirty-seven (37), valine (Val) is assigned prime number forty-one (41), tyrosine (Tyr) is assigned prime number forty-three (43), histidine (His) is assigned prime number forty-seven (47), alanine (Ala) is assigned prime number fifty-three (53), glutamate (Glu) is assigned prime number fifty-nine (59), glycine (Gly) is assigned prime number sixty-one (61), phenylalanine is assigned non-prime odd number twenty-five (25), and cysteine (Cys) is assigned non-prime odd number forty-five (45), and wherein prime and/or non-prime properties are identiified according to the z-number sums of Met and/or Ile headed amino acid sequences, Cys and/or Phe centered amino acid sequences, and heptad sequences within said protein or peptide, so as to determine the secondary and/or tertiary structure of said protein or peptide.

13. A method of determining secondary and/or tertiary structural properties of a protein or peptide comprising the following steps:

(a) determining the amino acid sequence of said protein or peptide;

(b) assigning each amino acid a z-number wherein tryptophan (Trp) is assigned non-prime odd number one (1), isoleucine (Ile) is assigned prime number two (2), methionine (Met) is assigned prime number three (3), threonine (Thr) is assigned prime number five (5), lysine (Lys) is assigned prime number seven (7), asparagine (Asn) is assigned prime number eleven (11), proline (Pro) is assigned prime number thirteen (13), leucine (Leu) is assigned prime number seventeen (17), glutamine (Gln) is assigned prime number nineteen (19), serine (Ser) is assigned prime number twenty-nine (29), aspartate (Asp) is assigned prime number thirty-one (31), arginine (Arg) is assigned prime number thirty-seven (37), valine (Val) is assigned prime number forty-one (41), tyrosine (Tyr) is assigned prime number forty-three (43), histidine (His) is assigned prime number forty-seven (47), alanine (Ala) is assigned prime number fifty-three (53), glutamate (Glu) is assigned prime number fifty-nine (59), glycine (Gly) is assigned prime number sixty-one (61), phenylalanine is assigned non-prime odd number twenty-five (25), and cysteine (Cys) is assigned non-prime odd number forty-five (45);

(c) delineating Met and/or Ile headed prime amino acid sequences by determining the length of sequences which begin with Met or Ile, wherein the sum of the z-numbers for the amino acids in such sequences is a prime number, and wherein the shortest sequence of such amino acids whose sum of z-numbers equal a prime number is determined;

(d) determining whether the Met and/or Ile headed prime amino acid sequences delineated in step (c) have a Cys or Phe in a center position;

(e) delineate Cys and/or Phe centered prime amino acid sequences by determining whether the sum of the z-numbers of the amino acid sequences immediately surrounding Cys and/or Phe are prime numbers, wherein such Cys and/or Phe are not in a center position of a Met or Ile headed prime amino acid sequence;

(f) delineate Cys and/or Phe residues present in the protein or polypeptide of step (a) wherein such Cys and/or Phe residues are not Cys and/or Phe residues according to steps (d) or (e);

(g) determining the length of the Met and/or Ile headed prime amino acid sequences of step (d) having a Cys and/or Phe in a center position;

(h) determining the length of the Cys and/or Phe centered prime amino acid sequences of step (e);

(i) delineating prime amino acid sequences according to step (e) wherein said amino acid sequence overlaps with a prime amino acid sequence according to step (c), and determining said prime amino acid sequences of step (e), which overlap, to be non-prime amino acid sequences;

j) identifying the crosslinking propensity, the propensity for forming fibrous, regular segments without turns or bends, and the propensity for forming segments which turn or bend, so as to determine the secondary or tertiary structure of the protein or peptide of step (a) wherein amino acid sequences according to steps (g) and (h) having a length>=seven amino acid residues have a propensity to crosslink with other such amino acid sequences, and wherein amino acid sequences according to steps (g) and (h) having a length<seven amino acid residues have a propensity to crosslink with other such amino acid sequences, and wherein amino acid sequences according to steps (f) and (i) have a propensity to crosslink with other such amino acid sequences.

14. A method according to claim 13, further comprising the following steps:

(a) for protein and/or peptide sequences beginning with Met, determine the z-number sums for sequential heptapeptide segments;

(b) for any heptapeptide segment having one Ile amino acid residue therein, determine the z-number sum for one additional amino acid residue, continuing in sequence so as to have a z-number sum of an octapeptide, and wherein when the z-number sum of this octapeptide is a prime number designate the sequence as a heptad, and continue as in step (a) wherein z-number sums for sequential heptapeptide segments are determined, and when the z-number sum is not a prime number, determine the z-number sum of one less amino acid sequence so as to have a z-number sum of a hexapeptide, and wherein when the z-number sum of this hexapeptide is a prime number designate the sequence as a heptad, and continue as in step (a) wherein z-number sums for sequential heptapeptide segments are determined, and when the z-number sum is not a prime number, delineate the heptapeptide segment having one Ile amino acid residue therein as having an even number z-number sum and continue as in step (a) wherein z-number sums for sequential heptapeptide segments are determined;

(c) delineating the number of heptapeptide and heptad segments having prime z-number sums;

(d) identifying the crosslinking propensity, the propensity for forming fibrous, regular segments without turns or bends, and the propensity for forming segments which turn or bend, as set forth in step (j) according to claim 2, and further, wherein segments of the protein or peptide having a high number of heptapeptide and heptad segments having prime z-number sums have a propensity to form fibrous, regular segments without turns or bends.

* * * * *